(12) United States Patent
Hamada et al.

(10) Patent No.: US 11,591,605 B2
(45) Date of Patent: Feb. 28, 2023

(54) PLANT GENOME EDITING METHOD

(71) Applicant: KANEKA CORPORATION, Osaka (JP)

(72) Inventors: Haruyasu Hamada, Hyogo (JP); Yozo Nagira, Hyogo (JP); Ryuji Miki, Hyogo (JP); Naoaki Taoka, Hyogo (JP); Ryozo Imai, Hokkaido (JP)

(73) Assignee: Kaneka Corporation, Osaka (JP)

( * ) Notice: Subject to any disclaimer, the term of this patent is extended or adjusted under 35 U.S.C. 154(b) by 9 days.

(21) Appl. No.: 16/189,225

(22) Filed: Nov. 13, 2018

(65) Prior Publication Data

US 2019/0062765 A1  Feb. 28, 2019

Related U.S. Application Data

(63) Continuation of application No. PCT/JP2017/018263, filed on May 15, 2017.

(30) Foreign Application Priority Data

May 13, 2016  (JP) .............. JP2016-097465

(51) Int. Cl.
*C12N 15/82* (2006.01)
*A01H 1/06* (2006.01)

(52) U.S. Cl.
CPC .......... *C12N 15/8207* (2013.01); *A01H 1/06* (2013.01); *C12N 15/8226* (2013.01); *C12N 15/8227* (2013.01); *C12N 15/8234* (2013.01)

(58) Field of Classification Search
CPC ............................................. C12N 15/8207
See application file for complete search history.

(56) References Cited

U.S. PATENT DOCUMENTS

| | | | |
|---|---|---|---|
| 5,736,369 A * | 4/1998 | Bowen ............... | C12N 15/8207 800/293 |
| 6,635,806 B1 | 10/2003 | Kriz et al. | |
| 6,858,777 B2 | 2/2005 | Zhong et al. | |
| 2002/0145010 A1 | 10/2002 | Ufheil et al. | |
| 2003/0110531 A1 | 6/2003 | Dan et al. | |
| 2008/0014633 A1 | 1/2008 | Spangenberg et al. | |
| 2012/0124696 A1 | 5/2012 | Ishida et al. | |
| 2012/0297506 A1 | 11/2012 | Dan et al. | |
| 2014/0068797 A1 | 3/2014 | Doudna et al. | |
| 2014/0176772 A1 | 6/2014 | Abe | |
| 2015/0267214 A1 | 9/2015 | Bendich et al. | |
| 2016/0208243 A1* | 7/2016 | Zhang ................ | C12N 15/111 |
| 2016/0297580 A1 | 10/2016 | Batzel et al. | |
| 2016/0355832 A1 | 12/2016 | Dan et al. | |
| 2017/0073670 A1 | 3/2017 | Nishida et al. | |
| 2017/0260535 A1* | 9/2017 | Xu ................ | C12N 15/8261 |
| 2018/0142248 A1* | 5/2018 | Martin-Ortigosa ........... C12N 15/8203 | |
| 2018/0223295 A1 | 8/2018 | Harling et al. | |
| 2019/0062765 A1 | 2/2019 | Hamada et al. | |
| 2019/0062766 A1 | 2/2019 | Hamada et al. | |

FOREIGN PATENT DOCUMENTS

| | | | |
|---|---|---|---|
| DE | 102015006335 | * 5/2015 | |
| DE | 102015006335 A1 | * 11/2016 | ............... A01H 5/04 |
| DE | 102015014252 A1 | * 5/2017 | ............... A01H 5/04 |
| DE | 102015014252 A1 | 5/2017 | |
| EP | 0 871 813 | 3/2003 | |
| JP | H10-503374 A | 3/1998 | |
| JP | 2002533057 A | 10/2002 | |
| JP | 2004-506427 | 3/2004 | |
| JP | 2004-527842 | 9/2004 | |
| JP | 2008-212048 | 9/2008 | |
| JP | 2010524474 A | 7/2010 | |
| JP | 2015-523856 A | 8/2015 | |
| JP | 2017-205103 | 11/2017 | |
| JP | 2017-205104 | 11/2017 | |
| WO | 95006127 A1 | 3/1995 | |
| WO | 9604392 A2 | 2/1996 | |
| WO | 2002/052025 A2 | 7/2002 | |
| WO | 2003007698 A2 | 1/2003 | |
| WO | 2005/024034 A1 | 3/2005 | |
| WO | 2011013764 A1 | 2/2011 | |
| WO | 2013/169802 A1 | 11/2013 | |
| WO | 2014065857 A1 | 5/2014 | |
| WO | 2014144987 A2 | 9/2014 | |
| WO | 2015/133554 A1 | 9/2015 | |
| WO | 2015171894 A1 | 11/2015 | |
| WO | 2017/090761 A1 | 6/2017 | |

OTHER PUBLICATIONS

Vianna et al (Fragment DNA as vector for genetic transformation of bean (*Phaseolus vulgaris* L.) Scientia Horticulturae 99, 371-378, 2004) (Year: 2004).*
Romano et al (Transformation of potato (*Solanum tuberosum*) using particle bombardment. Plant Cell Reports 20:198-204, 2001) (Year: 2001).*
Tillich (Seedling Diversity and the Homologies of Seedling Organs in the Order Poales (Monocotyledons). Annals of Botany 100:1413-1429, 2007). (Year: 2007).*
Lakshmanan et al (Rapid and Efficient Gene Delivery into Plant Cells Using Designed Peptide Carriers. Biomacromolecules, 14, 10-16, 2013). (Year: 2013).*

(Continued)

*Primary Examiner* — Charles Logsdon
*Assistant Examiner* — Wayne Zhong
(74) *Attorney, Agent, or Firm* — Hamre, Schumann, Mueller & Larson, P.C.

(57) ABSTRACT

A method for editing a plant genome includes coating a microparticle with at least one type of nucleic acid and/or at least one type of protein, introducing a deletion, insertion, or substitution into a target site in the genome of a plant by bombarding a shoot apex of the plant with the coated microparticle using a gene gun, growing the shoot apex bombarded with the coated microparticle to obtain a plant body, and selecting a genome-edited plant body from the plant body. The shoot apex of the plant is selected from the group consisting of a shoot apex of an embryo of a fully mature seed, a shoot apex of a young bud of a tuber, and a shoot apex of a terminal bud or a lateral bud.

20 Claims, 9 Drawing Sheets

Specification includes a Sequence Listing.

(56) References Cited

OTHER PUBLICATIONS

Sharma et al (APOBEC3A cytidine deaminase induces RNA editing in monocytes and macrophages. Nature communication, 1-15, Apr. 2015). (Year: 2015).*
Dhir et al (Optimization and transformation of Arundo donax L. using particle bombardment. African Journal of Biotechnology vol. 9, 6460-6469, 2010). (Year: 2010).*
Yang et al (Control of Rice Embryo Development, Shoot Apical Meristem Maintenance, and Grain Yield by a Novel Cytochrome P450. Molecular Plant. 6:1945-1960, 2013) (Year: 2013).*
Teper-Bamnolker et al (Release of Apical Dominance in Potato Tuber Is Accompanied by Programmed Cell Death in the Apical Bud Meristem. Plant Physiology, vol. 158, pp. 2053-2067, 2012). (Year: 2012).*
Takenaka et al (The process of RNA editing in plant mitochondria. Mitochondrion 8, 35-46, 2008) (Year: 2008).*
Mariam B. Sticklen et al., "Shoot apical meristem: A sustainable explant for genetic transformation of cereal crops", In Vitro Cellular & Development Biology—Plant; vol. 41, No. 3, pp. 187-200; May 1, 2005 (14 pages).
Kanniah Rajasekaran, "Biolistic Transformation of Cotton Zygotic Embryo Meristem", Transgenic Cotton: Methods and Protocols, Methods in Molecular Biology, vol. 958, pp. 47-57; Oct. 16, 2012 (11 pages).
C. Sautter et al., "Shoot apical meristems as a target for gene transfer by microballistics", Euphytica, Kluwer Academic Publishers, vol. 85, No. 1-3, pp. 45-51; Jan. 1, 1995 (7 pages).
Partial Supplementary European Search Report issued in corresponding European Application No. 17796264.4 dated Nov. 6, 2019 (15 pages).
E. L. Rech et al., "High-efficiency transformation by biolistics of soybean, common bean and cotton transgenic plants", Nature Protocols, 2008, vol. 3, No. 3, pp. 410-418 (9 pages).
R. Imai, "Genome editing in wheat-Development of an in planta transformation technique for direct introduction of editing enzymes", Agricultural biotechnology, Jan. 20, 2017, vol. 1, pp. 17-18 (4 pages).
R. Bilang et al., "Transient gene expression in vegetative shoot apical meristems of wheat after ballistic microtargeting," The Plant Journal, 1993, vol. 4, No. 4, pp. 735-744 (10 pages).
International Search Report issued in International Application No. PCT/JP2017/018263, dated Aug. 15, 2017 (2 pages).
Written Opinion of the International Search Authority issued in International Application No. PCT/JP2017/018263, dated Aug. 15, 2017 (9 pages).
R. Imai, "Genome editing in wheat-Development of an in planta transformation technique for direct introduction of editing enzymes," Agricultural Biotechnology, vol. 1, pp. 17-18, Jan. 20, 2017 (7 pages) with partial translation.
International Preliminary Report on Patentability issued in International Application No. PCT/JP2017/018263; dated Nov. 22, 2018 (16 pages).
A. Romano et al., "Transformation of potato (Solanum tuberosum) using particle bombardment," Plant Cell Reports, vol. 20, pp. 198-204, Feb. 20, 2001 (7 pages).
M. Lakshmanan et al., "Rapid and Efficient Gene Delivery into Plant Cells Using Designed Peptide Carriers," Biomacromolecules, vol. 14, pp. 10-16, 2013 (7 pages).
G. M. Chowrira et al., "Electroporation-Mediated Gene Transfer into Intact Nodal Meristems In Planta", Molecular Biotechnology, vol. 3, 1995, pp. 17-23 (7 pages).
https://micronmetals.com/products/tungsten-metal-powder/ retrieved Sep. 13, 2020. (Year: 2020).
R. M. Twyman et al., "Chapter 15: Plant Transformation Technology: Particle Bombardment", Handbook of Plant Biotechnology, 2004 (48 pages).
Office Action issued in U.S. Appl. No. 16/733,993, dated Sep. 23, 2020 (29 pages).

J.W. Kim et al., "Stable Delivery of a Canavalin Promoter-ß-Glucuronidase Gene Fusion into French Bean by Particle Bombardment," Plant Cell Physiol., 1997, vol. 38, No. 1, pp. 70-75 (6 pages).
J.W. Kim et al., "Transformation and regeneration of French bean plants by the particle bombardment process," Plant Science, 1996, vol. 117, pp. 131-138 (8 pages).
K. Lowe et al., "Germline Transformation of Maize Following Manipulation of Chimeric Shoot Meristems," Biotechnology, 1995, vol. 13, pp. 677-682 (6 pages).
G.S. Brar et al., "Recovery of transgenic peanut (Arachis hypogaea L.) plants from elite cultivars utilizing Accell® technology," The Plant Journal, 1994, vol. 5, No. 5, pp. 745-753 (9 pages).
T. Hasegawa et al., "Production of Transgenic Carnation Introduced Sarcotoxin Gene through Particle Bombardment," Research Bulletin of the Aichi-ken Agricultural Research Center, 2003, vol. 35, pp. 143-147 (6 pages).
H. Zhong et al., "The pea (Pisum sativum L.) rbcS transit peptide directs the Alcaligenes eutrophus polyhydroxybutyrate enzymes into the maize (Zea mays L.) chloroplasts," Plant Science, 2003, vol. 165, pp. 455-462 (8 pages).
Written Opinion of the International Search Authority issued in International Application No. PCT/JP2017/018262; dated Aug. 8, 2017 (6 pages).
P. Supartana et al. "Development of Simple and Efficient in Planta Transformation Method for Rice (Oryza sativa L.) Using Agrobacterium tumefaciens"; Journal of Bioscience and Bioengineering, vol. 100, No. 4, pp. 391-397; Jun. 2005 (7 pages).
International Preliminary Report on Patentability issued in International Application No. PCT/JP2017/018262; dated Nov. 22, 2018 (10 pages).
D.R. Russell et al., "Stable transformation of Phaseolus vulgaris via electric-discharge mediated particle acceleration," Plant Cell Reports, 1993, vol. 12, pp. 165-169 (5 pages).
H.D. Jones et al., "Wheat transformation: current technology and applications to grain development and composition"; Journal of Cereal Science, vol. 41, No. 2, pp. 137-147; Mar. 1, 2005 (11 pages).
F. Mahdavi et al., "Optimization of particle bombardment parameters for DNA delivery into the male flowers oh banana"; Biologia, vol. 69, No. 7, pp. 888-894; Jan. 1, 2014 (7 pages).
Extended European Search Report issued in corresponding European Application No. 17796263.6, dated Nov. 27, 2019 (9 pages).
C.P. Petrillo et al.,"Optimization of particle bombardment parameters for the genetic transformation of Brazilian maize inbred lines," Pesquisa Agropecuaria Brasileira, vol. 43, No. 3, pp. 371-378, Mar. 1, 2008 (8 pages).
European Office Action issued in corresponding European Application No. 17796263.6; dated Jul. 1, 2020 (6 pages).
T. Komiya; "Development of Apple Tissue Culture Techniques and Their Applications," Plant Tissue Culture Letters, vol. 9, issue 2, pp. 69-73; Jun. 19, 1992 (6 pages) with partial translation.
International Search Report issued in International Application No. PCT/JP2017/018262; dated Aug. 8, 2017 (3 pages).
Bulletin of Hokkaido Research Organization Agricultural Experiment Stations, "Introduction of the plasmid DNA by Electroporation into Potato Mesophyll Protoplasts," vol. 62, pp. 69-77, 1991, with English summary (9 pages).
Sailaja, M., et al., "Stable genetic transformation of castor (Ricinus communis L.) via particle gun-mediated gene transfer using embryo axes from mature seeds," Plant Cell Rep, vol. 27, pp. 1509-1519, 2008 (11 pages).
Office Action issued in corresponding Japanese Patent Application No. 2017-096886, dated Mar. 2, 2021, with English translation (10 pages).
Office Action issued in corresponding U.S. Appl. No. 16/733,993, dated Apr. 2, 2021 (34 pages).
Office Action issued in corresponding U.S. Appl. No. 16/189,442, dated Mar. 26, 2021 (35 pages).
Notification of Reasons for Refusal issued in Japanese Patent Application No. 2017-096887, dated Apr. 27, 2021 (14 pages).
Office Action issued in corresponding EP Application No. 17796264.4, dated Feb. 18, 2021 (6 pages).
Chlan et al., "A Procedure for Biolistic Transformation and Regeneration of Transgenic Cotton from Meristematic Tissue", Plant Molecular Biology Reporter, 1995, 7 pages.

(56) References Cited

OTHER PUBLICATIONS

Office Action issued in U.S. Appl. No. 16/189,442, dated Jul. 22, 2021, 26 pages.
Office Action issued in U.S. Appl. No. 16/733,993, dated Jul. 21, 2021, 28 pages.
Notice of Allowance issued in co-pending U.S. Appl. No. 16/733,993, dated Apr. 18, 2022, 21 pages.
Office Action issued in co-pending U.S. Appl. No. 16/189,442, dated Mar. 9, 2022, 19 pages.
Sharma, et al., "APOBEC3A cytidine deaminase induces RNA editing in monocytes and macrophages", Nature Communications, pp. 1-15, Apr. 21, 2015.
Dhir, et al, "Optimization and transformation of Arundo donax L. using particle bombardment", African Journal of Biotechnology, vol. 9, No. 39, pp. 6460-6469, Sep. 27, 2010.
Takenaka, et al., "The process of RNA editing in plant mitochondria", Mitochondrion, vol. 8, 2008, pp. 35-46.
Office Action issued in corresponding Australian Patent Application No. 2019300195, dated Apr. 29, 2022, 8 pages.
English translation of the Office Action issued in corresponding Japanese Patent Application No. 2021-500803, dated May 20, 2022, 5 pages.
Hamada, et al., "An in planta biolistic method for stable wheat transformation" Scientific Reports, 7:11443, Sep. 13, 2017, 8 pages.
International Search Report and Written Opinion issued in International Application No. PCT/JP2020/049058, dated Mar. 2, 2021, 20 pages w/translations.

\* cited by examiner

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: GFP forward primer

<400> SEQUENCE: 1
acggccacaa gttcagcgt                                                  19

<210> SEQ ID NO 2
<211> LENGTH: 19
<212> TYPE: DNA
<213> ORGANISM: Artificial Sequence
<220> FEATURE:
<223> OTHER INFORMATION: GFP reverse primer

<400> SEQUENCE: 2
accatgtgat cgcgcttct                                                  19

<210> SEQ ID NO 3
<211> LENGTH: 23
<212> TYPE: DNA
<213> ORGANISM: Artificial Sequence
<220> FEATURE:
<223> OTHER INFORMATION: TaMLO 20bp

<400> SEQUENCE: 3
ccgtcacgca ggacccaatc tcc                                             23

<210> SEQ ID NO 4
<211> LENGTH: 23
<212> TYPE: DNA
<213> ORGANISM: Artificial Sequence
<220> FEATURE:
<223> OTHER INFORMATION: TaQsd1 target

<400> SEQUENCE: 4
acggatccac ctccctgcag cgg                                             23

<210> SEQ ID NO 5
<211> LENGTH: 23
<212> TYPE: DNA
<213> ORGANISM: Artificial Sequence
<220> FEATURE:
<223> OTHER INFORMATION: TaLox2 target sequence

<400> SEQUENCE: 5
gtgccgcgcg acgagctctt cgg                                             23
```

<210> SEQ ID NO 6
<211> LENGTH: 21
<212> TYPE: DNA
<213> ORGANISM: Artificial Sequence
<220> FEATURE:
<223> OTHER INFORMATION: TaGASR7 target sequence

<400> SEQUENCE: 6
ccgccgggca cctacggcaa c                                              21

<210> SEQ ID NO 7
<211> LENGTH: 19
<212> TYPE: DNA
<213> ORGANISM: Artificial Sequence
<220> FEATURE:
<223> OTHER INFORMATION: TaQsd1-F primer

<400> SEQUENCE: 7
cagcctggag ggaatgacc                                                 19

<210> SEQ ID NO 8
<211> LENGTH: 19
<212> TYPE: DNA
<213> ORGANISM: Artificial Sequence
<220> FEATURE:
<223> OTHER INFORMATION: TaQsd1-R primer

<400> SEQUENCE: 8
acctggtgga atccagagc                                                 19

<210> SEQ ID NO 9
<211> LENGTH: 26
<212> TYPE: DNA
<213> ORGANISM: Artificial Sequence
<220> FEATURE:
<223> OTHER INFORMATION: TaLox2-F primer

<400> SEQUENCE: 9
cgtctaccgc tacgacgtct acaacg                                         26

<210> SEQ ID NO 10
<211> LENGTH: 26
<212> TYPE: DNA
<213> ORGANISM: Artificial Sequence
<220> FEATURE:
<223> OTHER INFORMATION: TaLox2-R primer

<400> SEQUENCE: 10
ggtcgccgta cttgctcgga tcaagt                                         26

<210> SEQ ID NO 11
<211> LENGTH: 22
<212> TYPE: DNA
<213> ORGANISM: Artificial Sequence
<220> FEATURE:
<223> OTHER INFORMATION: TaGASR7-F primer

<400> SEQUENCE: 11
ccttcatcct tcagccatgc at                                             22

<210> SEQ ID NO 12
<211> LENGTH: 23
<212> TYPE: DNA
<213> ORGANISM: Artificial Sequence
<220> FEATURE:
<223> OTHER INFORMATION: TaGASR7-R primer

```
<400> SEQUENCE: 12
ccactaaatg cctatcacat acg                                                 23

<210> SEQ ID NO 13
<211> LENGTH: 42
<212> TYPE: RNA
<213> ORGANISM: Artificial Sequence
<220> FEATURE:
<223> OTHER INFORMATION: NLS crRNA1

<400> SEQUENCE: 13
gugccgcgcg acgagcucuu guuuuagagc uaugcuguuu ug                            42

<210> SEQ ID NO 14
<211> LENGTH: 69
<212> TYPE: RNA
<213> ORGANISM: Artificial Sequence
<220> FEATURE:
<223> OTHER INFORMATION: tracrRNA

<400> SEQUENCE: 14
aaacagcaua gcaaguuaaa auaaggcuag uccguuauca acuugaaaaa guggcaccga         60
gucggugcu                                                                69

<210> SEQ ID NO 15
<211> LENGTH: 23
<212> TYPE: DNA
<213> ORGANISM: Artificial Sequence
<220> FEATURE:
<223> OTHER INFORMATION: Glyma 10G244400.1 20G150000.1 target

<400> SEQUENCE: 15
cctccgccca aggctccgcc acc                                                 23

<210> SEQ ID NO 16
<211> LENGTH: 42
<212> TYPE: RNA
<213> ORGANISM: Artificial Sequence
<220> FEATURE:
<223> OTHER INFORMATION: NLScrRNA gm 10G244400.1

<400> SEQUENCE: 16
gguggcggag ccuugggcgg guuuuagagc uaugcuguuu ug                            42

<210> SEQ ID NO 17
<211> LENGTH: 42
<212> TYPE: RNA
<213> ORGANISM: Artificial Sequence
<220> FEATURE:
<223> OTHER INFORMATION: crRNA2 rice OsPDS

<400> SEQUENCE: 17
guuggucuuu gcuccugcag guuuuagagc uaugcuguuu ug                            42

<210> SEQ ID NO 18
<211> LENGTH: 42
<212> TYPE: RNA
<213> ORGANISM: Artificial Sequence
<220> FEATURE:
<223> OTHER INFORMATION: crRNA3 apple PDS

<400> SEQUENCE: 18
accugaucga guaacuacag guuuuagagc uaugcuguuu ug                            42
```

```
<210> SEQ ID NO 19
<211> LENGTH: 42
<212> TYPE: RNA
<213> ORGANISM: Artificial Sequence
<220> FEATURE:
<223> OTHER INFORMATION: crRNA4 potato StIAA2

<400> SEQUENCE: 19
gauguuuagc uccuuuacua guuuuagagc uaugcuguuu ug                          42

<210> SEQ ID NO 20
<211> LENGTH: 42
<212> TYPE: RNA
<213> ORGANISM: Artificial Sequence
<220> FEATURE:
<223> OTHER INFORMATION: crRNA Zm ALS2

<400> SEQUENCE: 20
gcugcucgau uccgucccca guuuuagagc uaugcuguuu ug                          42

<210> SEQ ID NO 21
<211> LENGTH: 42
<212> TYPE: RNA
<213> ORGANISM: Artificial Sequence
<220> FEATURE:
<223> OTHER INFORMATION: crRNA barley HvPM19

<400> SEQUENCE: 21
gcucuccacu cugggcucuu guuuuagagc uaugcuguuu ug                          42
```

PLANT GENOME EDITING METHOD

TECHNICAL FIELD

One or more embodiments of the present invention relate to an in planta plant genome editing method with a particle bombardment method.

BACKGROUND

It is currently widespread as a general method of plant transformation that methods in which an exogenous gene is introduced into callus, or tissue piece of in vitro culture, via *Agrobacterium tumefaciens* or with a particle bombardment method. However even if a nuclease is introduced into a cell or a tissue so that a genome editing is made by such methods, it is difficult to regenerate a plant body to produce a genome-edited plant individual due to the difficulty in tissue culture for some plant species. Also, the introduction efficiency of gene or protein is not sufficiently high and therefore a selective marker gene has to be introduced to perform a marker selection for obtaining a transgenic individual. Furthermore, a somatic mutation (somaclonal mutation) often occurs with the need of long-term tissue culture. From the viewpoint of a reduction in the effort to produce a genetic modified plant and the safety of a transformed plant, there has been a demand for the development of an in planta genome editing method and a method for producing an in planta genome-edited individual without the involvement of tissue culture.

On the other hand, it is also known for wheat, rice, and the like that transformation methods without calluses or tissue pieces of in vitro culture (in planta transformation methods). As such an in planta transformation method, a method in which a gene is directly introduced into an exposed shoot apex of immature embryo or fully mature embryo with a particle bombardment method is used is known (Non-Patent Document 1). Moreover, Patent Document 1 and Non-Patent Document 2 disclose a method for infecting a fully mature embryo immediately after germination with *Agrobacterium* to introduce a gene.

However, the methods disclosed in these documents largely depend on the skill of an operator in common, so that gene transfer efficiency is low, and there is room for improvement of reproducibility. Moreover, in Non-Patent Document 1, it has not been demonstrated that the transgene is transmitted to a next generation. Due to these factors, the above-mentioned methods have not been widely used up to the present.

RELATED ART DOCUMENTS

Patent Documents

Patent Document 1: WO 2005/024034

Non-Patent Documents

Non-Patent Document 1: Bilang et al. Transient gene expression in vegetative shot apical meristems of wheat after ballistic microtargeting. Plant Journal (1993) 4, 735-744

Non-Patent Document 2: Supartana et al. Development of simple and efficient in planta transformation for rice (*Oryza sativa* L.) using *Agrobacterium tumefacienes*. Journal of Bioscience AND Bioengineering (2005) 4, 391-397

SUMMARY

One or more embodiments of the present invention provide a method for editing a plant genome without calluses or tissue pieces in in vitro culture.

The inventors have conducted intensive investigation and achieved one or more embodiments of the present invention.

That is, one or more embodiments of the present invention provide the followings:

(1) A method for editing a plant genome, comprising the steps of:
coating a microparticle with at least one type of nucleic acid and/or at least one type of protein;
bombarding a shoot apex of an embryo of a fully mature seed or a shoot apex of a young bud of a tuber with the coated microparticle using a gene gun;
growing the shoot apex bombarded with the coated microparticle to obtain a plant body; and
selecting a genome-edited plant body from the plant body.

(2) The method of (1), characterized by a step of bombarding into a L2 cell in the shoot apex of the embryo of the fully mature seed or the shoot apex of the young bud of the tuber.

(3) The method of (1), characterized by a step of bombarding into a shoot apical stem cell that transits to a germ cell line in the shoot apex of the embryo of the fully mature seed or the shoot apex of the young bud of the tuber.

(4) The method as described in any one of (1) to (3), characterized in that the microparticle has a diameter of 0.3 µm or more and 1.5 µm or less.

(5) The method as described in any one of (1) to (4), wherein the shoot apex of the embryo in the fully mature seed is an exposed shoot apex in which an endosperm, a coleoptile, a leaf primordium, and an excess of scutellum are removed from the fully mature seed.

(6) The method as described in any one of (1) to (4), wherein the shoot apex of the young bud of the tuber is an exposed shoot apex in which a tuber and a leaf primordium is removed from the young bud of the tuber.

(7) The method as described in any one of (1) to (5), characterized in that the fully mature seed is a fully mature seed having a root in length of 1 mm or less.

(8) The method as described in any one of (1) to (7), characterized in that the plant is any one selected from the group consisting of wheat, barley, rice, corn, soybean, potato, and apple.

(9) The method as described in any one of (1) to (8), characterized in that the nucleic acid comprises a nucleic acid encoding a modification enzyme.

(10) The method as described in any one of (9), characterized in that the modification enzyme is a nuclease or a deaminase.

(11) The method as described in any one of (1) to (10), characterized in that the nucleic acid comprises a nucleic acid capable of expressing at least one guide RNA and a nucleic acid encoding a Cas nuclease protein, being linked to a promoter and a terminator so that each is expressed.

(12) The method as described in any one of (1) to (11), wherein the protein is a nuclease.

(13) The method as described in any one of (1) to (12), wherein the protein is a Cas nuclease.

(14) A method for producing a genome-edited plant body using the method of any one of (1) to (13).

(15) A method for editing a plant genome, comprising the steps of:
coating a microparticle with a diameter of 0.3 µm or more and 1.5 µm or less with at least one type of nucleic acid and/or at least one type of protein;

bombarding a shoot apex of an embryo in a fully mature seed with the coated microparticle using a gene gun;

growing the shoot apex bombarded with the coated microparticle to obtain a plant body; and selecting a genome-edited plant body from the plant body.

(16) The method of (15), wherein the shoot apex of the embryo in the fully mature seed is an exposed shoot apex in which an endosperm, a coleoptile, a leaf primordium, and an excess of scutellum are removed from the fully mature seed.

(17) The method as described in. (15) or (16), characterized in that the fully mature seed is a fully mature seed having a root in length of 1 mm or less.

(18) The method as described in any one of (15) to (17), characterized in that the plant is any one selected from the group consisting of wheat, rice, corn, and soybean.

(19) The method as described in any one of (15) to (18), characterized in that the nucleic acid comprises a nucleic acid encoding a nuclease.

(20) The method as described in any one of (15) to (19), characterized in that the nucleic acid comprises a nucleic acid capable of expressing at least one guide RNA and a nucleic acid encoding a Cas nuclease protein, being linked to a promoter and a terminator so that each is expressed.

(21) The method as described in any one of (15) to (18), wherein the protein is a nuclease.

(22) The method as described in any one of (15) to (18), wherein the protein is a Cas nuclease.

(23) A method for producing a genome-edited plant body using the method as described in any one of (15) to (22).

(24) A method for editing a genome of a germ cell line or a stem cell that can shift to the germ cell line in a shoot apical meristem using an in planta method.

(25) The method of (24), characterized by comprising the method of any one of (1) to (13).

(26) A method for producing a genome-edited plant body using the method as described in (24) or (25).

(27) A genome-edited plant body produced by the production method of (26) (excluding those known at the time of filing).

According to the method of one or more embodiments of the present invention, a shoot apex is used as a target of a particle bombardment method, thus making it possible to editing a plant genome with good reproducibility without the need for callus formation and a selective marker gene. According to one or more embodiments of the present invention, it is possible to make genome editing of shoot apical stem cells that transit to a germ cell lines in a shoot apex.

DETAILED DESCRIPTION OF EMBODIMENTS

Figure 1:
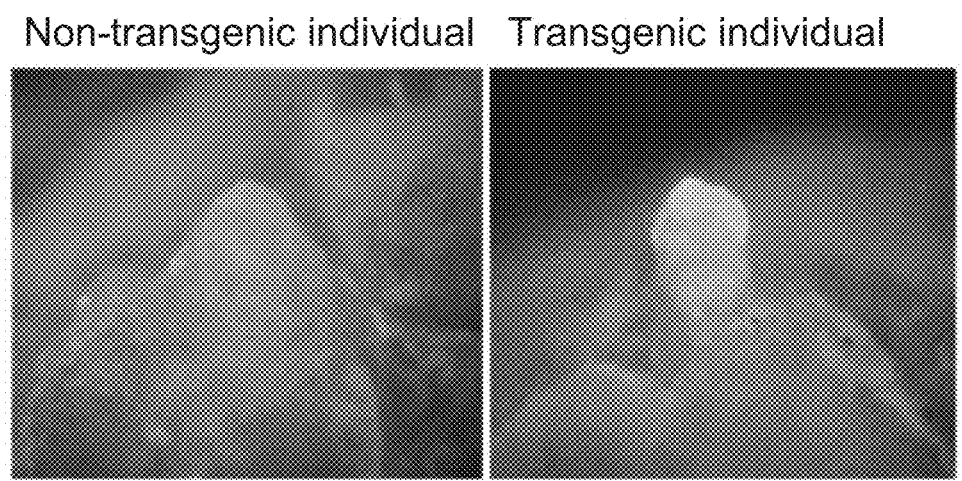
FIG. 1 is a diagram showing the appearance of GFP protein expression in a shoot apex in Example 1 according to one or more embodiments of the present invention.

Hereinafter, one or more embodiments of the present invention will be described in detail.

An in planta genome editing method according to one or more embodiments of the present invention includes steps of allowing a fully mature seed of a plant to absorb water; and then exposing a shoot apex of an embryo in the seed; and then editing the genome of a cell of the shoot apex.

The "genome editing" as used herein is a portion of the techniques called "new breeding techniques (NBT)", and includes, but not be limited to, disrupting a gene by cleaving a specific gene on a genome and introducing a mutation thereinto, or inserting or substituting a DNA fragment in a site-specific manner, using a meganuclease, CRISPR-CAS, or the like; or introducing a point mutation of interest with a high efficiency to modify a gene function by constructing an artificial enzyme complex via removing nuclease activity from the CRISPR system and adding thereto a deamination enzyme, deaminase, and expressing the complex in a cell, and the technique may be used as far as a genome can be edited therewith. Using the genome editing technique makes it possible to disrupt a gene of interest with a high efficiency. With the gene disruption, a gene of interest can be only disrupted without traces of gene recombination, and therefore, such gene-disrupted plants are not treated as recombinant plants in some countries. Moreover, with the genome editing, site-specific insertion or substitution of a DNA fragment can be efficiently performed by linking the respective fragments that are homologous to the respective sequences of the two sides of a cleaved sequence to the two sides of a DNA fragment to be introduced into that site, respectively.

In the sense described above, the genome editing can be regarded as a technique different from a conventional plant transformation method, such as a direct introduction method or an *Agrobacterium* mediated method, in which an exogenous gene is incorporated in a substantially random manner. The genome editing technique has a feature of including a step of cleaving a genome DNA using a nuclease capable of targeting a cleavage site, or a nuclease with a guide RNA and can be distinguished from a conventional transformation method without a nuclease capable of targeting, or a nuclease with a guide RNA. The term "using a nuclease, or a nuclease with a guide RNA" as used herein means that a nuclease protein may be introduced into a cell, and a DNA and/or RNA encoding a nuclease gene may be introduced into a cell to express a nuclease protein. Also, regarding the guide RNA, it is construed that an RNA may be introduced into a cell, and a DNA capable of expressing a guide RNA may be introduced to express a guide RNA.

The "seed" as used herein encompasses not only a natural seed obtained by cultivating (or culturing) a plant under nature conditions or conditions close to natural conditions but also an artificial seed. In one or more embodiments, a natural seed is preferable. However, if an artificial seed from which a transformable shoot apex can be obtained is developed, such an artificial seed can be used. The natural seed includes not only a seed obtained in an outdoor field or the like, but also a seed obtained through greenhouse cultivation and a seed obtained from a tissue culture such as an in vitro seedling. A seed obtained through tissue culture such as a direct reprogramming, or the like can also be used as the seed according to one or more embodiments of the present invention as long as a shoot apex can be obtained therefrom.

In one or more embodiments of the present invention, it is preferable to use a fully mature seed or a subterranean stem as a material to obtain a shoot apex. The "fully mature seed" refers to a seed that comes into full maturity in which the process of maturing after pollination is completed. The "subterranean stem" collectively refers to stems in the underground, including a tuber, which is a lump and has a plurality of buds; a corm, which is in a spherical shape and has a large terminal bud; and a bulb, which is in a spherical shape and has enlarged scaly leaves being attached to a shortened stem.

The "shoot apex" as used herein encompasses a growing point (shoot apical meristem) at the leading end of a stem, and a tissue including the growing point and several leaf primordia derived from the growing point. In one or more embodiments of the present invention, only a hemispherical (dome-shaped) growing point obtained by removing leaf primordia may be used as a shoot apex, or a shoot apex including a growing point and leaf primordia or a plant tissue including such a shoot apex may be used. A virus-free tissue is obtained by using only a growing point obtained by removing leaf primordia. Moreover, the "germ cell line" as used herein collectively refers to germ cells ranging from a primordial germ cell, which is the origin of a germ cell, to an oocyte and a spermatoblast, which are end products, and the "L2 layer" refers to the second cell layer from the outermost layer in a shoot apical meristem.

1. Step of Pre-Treatment for Genome Editing

The in planta genome editing method according to one or more embodiments of the present invention can be applied to a wide variety of common seed-producing plants, plants that produces subterranean stems, and plants that can be subjected to shoot apex culture. Therefore, plants to be subjected to the in planta genome editing method according to one or more embodiments of the present invention are spermatophytes including angiosperms and gymnosperms. Angiosperms include monocotyledons and dicotyledons. In general, an in planta genome editing method is a method of editing the genome of cells in a growing point in a plant growing state, without an operation for tissue culture. However, the "in planta genome editing method" as used herein only encompasses those including a tissue culture method associated with shoot apex culture, but does not encompass those including any operation for other tissue cultures. Same applies to an in planta method.

There is no limitation on the type of monocotyledon, and examples thereof include plants of Gramineae, Liliaceae, Musaceae, Bromeliaceae, and Orchidaceae.

Examples of the plants of Gramineae include rice, wheat, barley corn, oat, Japanese lawn grass, sorghum, rye, millet, and sugar cane. Examples of the plants of Liliaceae include Welsh onion and asparagus. An example of the plants of Musaceae is banana. An example of the plants of Bromeliaceae is pineapple. Examples of the plants of Orchidaceae include orchids.

Examples of the dicotyledons include plants of Brassicaceae, Leguminosae, Solanaceae, Cucurbitaceae, Convolvulaceae, Rosaceae, Moraceae, Malvaceae, Asteraceae, Amaranthaceae, and Polygonaceae.

Examples of the plants of Brassicaceae include thale cress, Chinese cabbage, rape, cabbage, cauliflower, and Japanese radish. Examples of the plants of Legumineae include soybean, red mung bean, kidney bean, pea, black-eyed pea, and alfalfa. Examples of the plants of Solanaceae include tomato, eggplant, potato, tobacco, and red pepper. Examples of the plants of Cucurbitaceae include Oriental melon, cucumber, cantaloupe melon, and watermelon. Examples of the plants of Convolvulaceae include morning glory sweet potato (yam), and bindweed. Examples of the plants of Rosaceae include roses, strawberry and apple. Examples of the plants of Moraceae include mulberry fig, and rubber tree. Examples of the plants of Malvaceae include a cotton plant and kenaf. An example of the plants of Asteraceae is lettuce. An example of the plants of Amaranthaceae is beet (sugar beet). An example of the plants of Polygonaceae is buckwheat.

On the other hand, examples of the gymnosperms include pine, Japanese cedar, ginkgo, and cycad.

In an embodiment of the in planta genome editing method according to one or more embodiments of the present invention, first, a fully mature seed of a plant is allowed to absorb water. A fully mature seed may be vernalized as necessary before allowed to absorb water. A seed is allowed to absorb water by soaking and incubating the seed with water. In one or more embodiments, the water absorption temperature is preferably 15 to 25° C. for wheat, barley or rice, and preferably 25 to 35° C. for corn or soybean, for example. At this time, water may be replaced one or more times. Regarding the water absorption period, in the case of wheat, for example, it may be preferable to allow a seed to absorb water until before a radicle starts growing or until before a new leaf primordium is formed. When the water absorption period is expressed by amount of time for water absorption, a seed may be allowed to absorb water for less than 16 hours after the start of the water absorption, and preferably 12 hours, depending on the dormant state of the seed. This water absorption step allows the seed to be softened, thus making it easy to expose a shoot apex.

2. Step of Exposing Shoot Apex of Embryo in Seed

Then, a shoot apex of an embryo in the seed that has been allowed to absorb water as described above is exposed. For wheat, barley rice, or corn, a shoot apex is exposed by removing coleoptiles and leaf primordia. For soybean, a shoot apex is exposed by removing a seed coat and cotyledons. For potato, a shoot apex is exposed by allowing a seed potato to sprout and removing leaf primordia from an isolated young bud. For apple, a shoot apex is exposed by removing leaf primordia from a seed embryo, or an isolated terminal bud or lateral bud. The means for exposing can be any means as long as a coleoptile and a leaf primordium, or a seed coat and a cotyledon can be removed therewith under a stereoscopic microscope, and examples of the means include punching tools such as a needle with a diameter of about 0.2 mm, tweezers, pipettes, syringes, and cutting tools such as a scalpel and a cutter. Then, an endosperm and an excess portion of a scutellum are removed by use of a cutting tool such as a scalpel, and the embryo, including the exposed shoot apex, and the scutellum are placed on an agar medium so that the shoot apex faces upward. In order to obtain a virus-free shoot apex, a scalpel may be replaced by a freshly sterilized scalpel at a final stage to isolate the shoot apex. In this case, a virus-free plant body can be obtained.

3. Step of Introducing Nucleic Acid and/or Protein into Cells of Shoot Apex

There is no particular limitation on a technique for introducing an intended gene such as a site-directed nuclease, and a known genetic engineering technique can be used. In general, a recombinant vector containing an intended gene is produced, and a nucleic acid (e.g., recombinant vector) or a protein can be introduced into a shoot apex of a fully mature embryo as a target using an *Agrobacterium*-mediated method, an electroporation method, a particle bombardment method, a PEG-calcium phosphate method, a liposome method, a microinjection method, a whisker method, a plasma method, a laser injection method, or the like. For wheat, rice, corn, or soybean, a method for introduction into an embryo of a fully mature seed with a particle bombardment method may be preferable from the viewpoint of transfer efficiency into a plant body. The particle bombardment method is also effective in introducing a gene into a potato shoot apex. The particle bombardment method is a method of bombarding a cellular tissue with metal microparticles coated with a nucleic acid and/or a protein, and is effective for a case where *Agrobacterium* infection efficiency is low, such as a case of monocotyledons.

There is no particular limitation on a vector used in one or more embodiments of the present invention, and examples thereof include pAL-based vectors (e.g., pAL51 and pAL156), pUC-based vectors (e.g., pUC18, pUC19, and pUC9), pBI-based vectors (e.g., pBI121, pBI101, pBI221, pBI2113, and pBI101.2), pPZP-based vectors, pSMA-based vectors, intermediate vectors (e.g., pLGV23 Neo and pNCAT), cauliflower mosaic virus (CaMV), bean common mosaic virus (BGMV), and tobacco mosaic virus (TMV).

A vector containing an intended gene can be produced as described below, for example. In order to insert an intended gene into a vector a method can be used in which a purified DNA is cleaved with an appropriate restriction enzyme, inserted into a restriction enzyme site or multicloning site of an appropriate vector DNA and ligated to the vector. An intended gene may be inserted into an intermediate vector through double cross-over. TA cloning, In-Fusion coning, and the like may also be used.

There is no particular limitation on a gene of target for genome editing as long as the destruction of the gene or the insertion or substitution of the gene is desired. A nuclease gene to be introduced may be derived from species of different organism, and the genes may be derived from animals, plants, microorganisms, viruses, or the like, and an artificially synthesized gene can be used, for example. Examples of such a gene include a meganuclease gene, TALEN, CRISPR-CAS system, and TARGET AID.

There is no particular limitation on a gene to be targeted for genome editing. Examples of such a gene include glycometabolism related genes, lipid metabolism related genes, useful substance (e.g., medicine, enzyme, pigment, and aroma component) producing genes, plant growth controlling (promoting/inhibiting) related genes, flowering regulation related genes, disease-and-pest resistance (e.g., insect damage resistance, nematode disease resistance, mold (fungus) disease resistance, bacterial disease resistance, and virus (disease) resistance) related genes, environmental stress (e.g., low temperature, high temperature, dryness, salt, photoinhibition, and ultraviolet rays) resistance related genes, transporter related genes, flour milling properties related genes, baking properties related genes, noodle-making properties related genes, and genes related to enzyme for recombination.

An exogenous DNA may be inserted into the site of cleavage or substituted between the sites of cleavage in a target gene for genome editing via a recombination so as to introduce an intended mutation.

Examples of proteins encoded by the site-specific nuclease genes include a zinc finger nuclease, a protein expressing zinc finger nuclease activity and a TAL effector nuclease (TALLEN). The zinc finger nuclease is a fusion protein of several zinc finger motifs that recognize a specific base and a FokI nuclease. The TALLEN is a fusion protein of a Transcription Activator Like (TAL) effector and a FokI nuclease. A site-specific nuclease includes another additional targeting technology such as a meganuclease, RNA inducible CRISPR-Cas9, or a leucine zipper.

Editing a genome by introducing a site-specific nuclease into a shoot apex using a gene gun makes it possible to change or modify the expression of one or more gene products. Specifically for a cell that may contain and express a DNA molecule encoding one or more gene products, a CRISPR-Cas system which may contain a Cas protein and one or more guide RNAs targeting the DNA molecule is introduced into the cell, so that the one or more guide RNAs target genome gene loci of the DNA molecule encoding the one or more gene products, and the Cas protein cleaves the genome gene loci of the DNA molecule encoding the one or more gene products, thus making it possible to change or modify the expression of the one or more gene products.

When a genome is edited by introducing a nuclease gene or a nuclease protein into a cell using a gene gun, a stable transformant is not necessarily formed through integration with the genome. A genome can be edited through transient expression of a nuclease gene. A genome can be also edited by introducing a protein (and a guide RNA) into a cell. With these methods, the obtained genome-edited individual is not a genetic modified organism in some cases.

Cas protein and a guide RNA may be used in a naturally occurring manner (in combination), or may be used in combination that is not present in nature. In one or more embodiments of the present invention, the expression of two or more gene products may be changed or modified. The guide RNA may include a guide sequence fused to a tracr sequence.

The guide RNA has a length of at least 15, 16, 17, 18, 19, or 20 nucleotides. In one or more embodiments, the maximum of nucleotide length is preferably 30 or less, more preferably 25 or less, even more preferably 22 or less, and the most preferably 20 or less.

In one or more embodiments, a cell to be subjected to genome editing is a plant cell, further preferably a cell in a shoot apical meristem, and the most preferably a cell that transits to a germ cell line in a shoot apical meristem.

In one or more embodiments of the present invention, the Cas protein may contain one or more nuclear localization signals (NLSs). In some embodiments, the Cas protein is a type-II CRISPR enzyme. In some embodiments, the Cas protein is a Cas9 protein. In some embodiments, the Cas9 protein is Cas9 of Streptcoccus pneumoniae (S. pneumoniae), Streptcoccus pyogenes (S. pyogenes), or Streptcoccus thermophilus (S. thermophilus), and may also encompass mutant Cas9 derived from these organisms. The protein may be a Cas9 homolog or a Cas9 ortholog.

The Cas protein may be subjected to codon optimization for the expression in a eucaryotic cell. The Cas protein may direct the cleavage of one or two strands at a position where a target sequence is localized. In one or more embodiments of the present invention, the expression of a gene product is reduced, and the gene product is a protein.

In addition to an intended gene, a promoter an enhancer, an insulator, an intron, a terminator, a poly A addition signal, a selective marker gene, and the like can be ligated to the vector.

A plurality of types of intended genes may be inserted into a single vector, or a single microparticle may be coated with a plurality of types of recombinant vectors. For example, a recombinant vector containing a nuclease gene and a recombinant vector containing a drug resistance gene may be separately produced, and these recombinant vectors may be coated on microparticles in combination, and a plant tissue may be bombarded with such microparticles.

Genome editing may be directed to two or more genes. A vector may be constructed such that two or more directed genes can be cleaved. In this case, two or more of vectors may be produced, or a plurality of guide RNAs may be inserted into a single plasmid so that they are expressed, respectively. The guide RNA may include a guide sequence fused to a tracr sequence.

Site-directed genome editing may be performed by cleaving a double strand in a site-directed manner and promoting homologous recombination through genome editing. In this case, a DNA including the respective sequences that are homologous to the two sides of a cleaved region may be introduced to induce a double cross-over. Also, a Cas9 D10A mutant, which is known to function as a nickase (a DNA nicking enzyme that nicks only one DNA strand), can be used to induce homologous recombination.

A promoter that is not derived from a plant may be used as long as a promoter is a DNA that can function in a plant body or a plant cell, and direct a constitutive expression or an expression in a specific tissue of a plant or at a specific growth stage of a plant. Specific examples thereof include a cauliflower mosaic virus (CaMV) 35S promoter, an E12-35S omega promoter a promoter of nopaline synthase gene (Pnos), a ubiquitin promoter derived from corn, an actin promoter derived from rice, a PR protein promoter derived from tobacco, an ADH promoter, and a RuBisco promoter. A sequence that enhances translational activity such as an omega sequence of a tobacco mosaic virus can be used to enhance the translation efficiency. Moreover, IRES (internal ribosomal entry site) can be inserted into a site on the 3' downstream side of a promoter and the 5' upstream side of a translation initiation codon as a translation initiation region to translate a protein from a plurality of coding regions.

The terminator is a sequence that can terminate the transcription of a gene transcribed by the above-mentioned promoter, and contains a poly A addition signal, and examples of the terminator include the terminator of a nopaline synthase (NOS) gene, the terminator of an octopine synthase (OCS) gene, and a CaMV 35S terminator.

Examples of the selective marker gene include herbicide resistance genes (e.g., a bialaphos resistance gene, a glyphosate resistance gene (EPSPS), and a sulfonylurea resistance gene (ALS)), drug resistance genes (e.g., a tetracycline resistance gene, an ampicillin resistance gene, a kanamycin resistance gene, a hygromycin resistance gene, a spectinomycin resistance gene, a chloramphenicol resistance gene, and a neomycin resistance gene), fluorescence or luminescence reporter genes (e.g., luciferase, β-galactosidase, β-glucuronidase (GUS), and green fluorescent protein (GFP)), and enzyme gene such as a neomycin phosphotransferase II (NPT II) and dihydrofolate reductase. However, with one or more embodiments of the present invention, a genome-edited plant can be produced without introducing a selective marker gene.

A vector containing a nuclease for targeting a directed gene as mentioned above is bombarded into a fully mature embryo of wheat using a particle bombardment method. The nucleic acid encoding a nuclease gene and/or protein (e.g., a nuclease) for targeting a directed gene can be coated on the surface of microparticles (microcarriers) and such microparticles (microcarriers) can be bombarded into plant cells using a gene gun. Metal microparticles are favorably used as the microparticles because they have high specific gravity to improve a cell penetration power, and they are chemically inert and thus less likely to harm a living organism. Gold particles, tungsten particles, and the like are particularly favorably used among the metal microparticles.

In the particle bombardment method, an intended gene can be introduced into a plant cell as follows. First, microparticles such as gold particles or tungsten particles are washed and sterilized, and a nucleic acid (e.g., recombinant vector linear DNA, or RNA) and/or a protein, $CaCl_2$ and spermidine are added to the microparticles while being stirred using a vortex mixer or the like so that the gold particles or tungsten particles are coated with the DNA or RNA and/or a protein, and then the particles are washed with ethanol, phosphate buffered saline (PBS), or the like.

In one or more embodiments, the particle diameter (diameter) of the microparticles is preferably 0.3 µm or more and 1.5 µm or less, more preferably 0.4 µm or more, even more preferably 0.5 µm or more, and especially preferably 0.6 µm. In one or more embodiments, the maximum particle diameter is preferably 1.4 µm or less, more preferably 1.3 µm or less, even more preferably 1.2 µm or less, especially preferably 1.1 µm or less, and the most preferably 1.0 µm or less.

The gold particles or tungsten particles are applied onto a macrocarrier film using Pipetman or the like as uniformly as possible and then dried in a sterile environment such as a clean bench. When microparticles coated with a protein are used, it may be preferable to use a hydrophilic macrocarrier film.

A hydrophilic macrocarrier film may be formed by attaching a hydrophilic film to a macrocarrier film or applying hydrophilic coating onto a macrocarrier film. Examples of an approach for the hydrophilization of a film include approaches by use of a surfactant, a photocatalyst, a hydrophilic polymer, or the like.

Examples of the hydrophilic polymer used in the above-mentioned approach include polymers of a hydrophilic monomer such as polyethylene glycol, hydroxyethyl methacrylate, hydroxypropyl methacrylate, dihydroxyethyl methacrylate, diethylene glycol methacrylate, triethylene glycol methacrylate, polyethylene glycol methacrylate, vinylpyrrolidone, acrylic acid, acrylamide, dimethylacrylamide, glucoxyoxyethyl methacrylate, 3-sulfopropylmethacryloxyethyldimethylammonium betaine, 2-methacryloyloxyethyl phosphorylcholine, or 1-carboxydimethylmethacryloyloxyethyl methaneammonium.

And, the macrocarrier film and a plate on which a targeted shoot apex of a fully mature embryo is placed are mounted in a particle bombardment apparatus, and then a high-pressure helium gas is shot from a gas accelerating tube toward the macrocarrier film. The macrocarrier film stops at a stopping plate, but the gold particles pass through the stopping plate and enter the target placed below the stopping plate, so that the intended gene is introduced thereinto.

Depending on the particle diameter of the microparticles, the distance between the stopping plate and the targeted shoot apex may be preferably 9 cm or less, more preferably 8 cm or less, even more preferably 7 cm or less, and especially preferably 6 cm or less, for example, and the minimum distance may be preferably 2 cm or more, more preferably 3 cm or more, and even more preferably 4 cm or more, for example. Regarding the distance between the stopping plate and the target, an optimum value can be determined as appropriate through transient expression experiment or the like depending on the type of microparticles, the particle diameter, gas pressure, and the like.

In one or more embodiments, the gas pressure is preferably 1,100 to 1,600 psi, and more preferably 1,200 to 1,500 psi, for example, depending on the type of microparticles and the distance to the target. Regarding the gas pressure, an optimum value can be determined as appropriate through transient expression experiment or the like depending on the type of microparticles, the type of target, the distance between the target and the stopping plate, and the like.

In one or more embodiments of the present invention, the number of shot for bombarding a shoot apex with the microparticles is preferably two shots or more, more preferably three shots or more, and even more preferably four shots or more. In one or more embodiments, the upper limit of shot for bombarding a shoot apex with the microparticles is preferably twenty shots or less, more preferably fifteen shots or less, and even more preferably ten shots or less. Regarding the number of shot for bombardments, an optimum number is determined as appropriate through transient expression experiment or the like.

In the cell bombarded with the microparticles, the nucleic acid and/or the protein is released from the microparticle. The nucleic acid is transferred into a nucleus to express a nuclease so that a genome DNA is cleaved, and a mutation is induced in the process of repairing and a genome-edited cell is thus obtained. The protein is transferred to a nucleus (organelle) with a nuclear localization signal (optionally an organelle localization signal), and it cleaves a DNA and the genome editing is thus generated. Genome editing can be applied to not only genomic genes of a nucleus but also genes of organelles (intracellular organelles such as a chloroplast and mitochondria). In this case, a certain organelle localization signal linked to a nuclease may be introduced, or a promoter that is expressed only in a certain organelle may be linked to a nuclease.

The shoot apex of a fully mature embryo in which a nuclease is introduced and a genome editing is made is grown on an agar medium for about a month and then transferred to soil. A bombarded shoot apex can be grown on a normal medium without applying selective pressure using a drug or the like (i.e., on a medium free from antibiotics or the like) to obtain a genome-edited plant individual, but a drug resistance gene can be introduced with a nuclease so as to select a genome-edited plant individual. When a drug resistance gene is introduced, a drug can be used to selectively culture cells in which a nuclease gene and/or a nuclease is introduced. For example, a sulfonylurea-based herbicide, chlorsulfuron (the resistance against this herbicide can be acquired by introducing a mutated ALS gene (acetobutyrate synthase gene)), or the like is known as a selection drug suitable for shoot apex culture.

When a drug resistance gene is introduced, the drug resistance gene and the nuclease gene may be present in the same vector or separate vectors. When the drug resistance gene and the target gene are inserted into separate vectors, and are integrated into separate chromosomes, there is an advantage that self-pollination or backcross is performed to produce progenies so that a genome-edited plant individual and a drug resistance gene-carrying plant individual can be separately obtained.

With the above-described method, a plant body in which a genome editing is made for a directed gene can be created. In the thus created plant, the trail of a stably genome-edited gene is expressed or the expression of the directed gene is suppressed, which is normally inherited (transmitted) to progenies.

The gene transfer efficiency into wheat and the genome editing efficiency can be evaluated as follows.

For the gene transfer efficiency a DNA is extracted from a grown individual that has been subjected to a gene introduction process, and whether or not a genome editing of the directed gene has been made can be detected by PCR and/or Southern blotting. The genome editing efficiency is calculated from the number of explants used for the introduction and the number of grown individuals carrying an exogenous gene.

For the genome editing efficiency of the directed gene, the presence or absence of an RNA expressed from the directed gene is evaluated for the grown individual in which the gene introduction has been confirmed. The presence or absence of an RNA can be confirmed using an RT-PCR method, for example. It may be detected through Northern blotting.

Also, the presence or absence of a protein expressed from the genome-edited directed gene can be evaluated. The presence or absence of a protein can be confirmed through staining of plant section, electrophoresis, ELISA, RIA, dot-immunobinding assay and/or Western blotting, for example. The genome editing efficiency of the directed gene is calculated from the number of explants used for the gene introduction and the number of grown individuals in which the presence (or absence) of a protein by genome editing of the directed gene has been confirmed.

EXAMPLES

Hereinafter, one or more embodiments of the present invention will be specifically described by way of examples, but the present invention is not limited to the examples.

Example 1: Investigation of Gold Particle Diameter Optimum for Gene Introduction In order to determine a suitable gold particle diameter the presence or absence of GFP fluorescence in a shoot apex that had been subjected to a gene introduction process or the presence or absence of a transgene in a current generation ($T_0$ generation) was examined.

1. Study Using Transient Expression System of GFP Fluorescent Protein as Index (1) Preparation of Fully Mature Seed of Wheat Fully mature seeds of wheat (*Triticum aestivum* cv. Fielder) were immersed in Haiter (a hypochlorous acid concentration of 6%; manufactured by Kao Corporation), shaken at room temperature for 20 minutes, and washed with sterile water in a clean bench. After having been washed, the seeds were placed on Kimtowel or filter paper moistened with sterile water, and incubated at 4° C. for 2 days for the breaking dormancy. Thereafter, the seeds were incubated at 22° C. for about 12 hours and then used in the following experiments.

(2) Exposure of Shoot Apex in Embryo of Fully Mature Seed

A coleoptile and the first to third leaf primordia in the embryonic moiety of each of the above-mentioned germinated seeds were removed using a leading end of a needle (with a diameter of 0.20 mm) under a stereoscopic microscope. Thereafter, an endosperm and an excess portion of a scutellum were removed using a sterile knife (or a sterile scalpel), and the shoot apex moiety was thus fully exposed. The thus obtained samples were placed on an MS-maltose medium (4.3 g/L MS salt, MS vitamin, 30 g/L maltose, 0.98 g/L MES, 3% PPM (plant preservative mixture; Nacalai Tesque Inc.), 7.0 g/L phytagel (registered trademark; Sigma-Aldrich), pH 5.8) at 30 samples per plate.

(3) Gene Introduction

The gene introduction into the shoot apex of the fully mature embryo of wheat was performed using a particle bombardment method as described below.

In this example, it was used that a plasmid DNA (pUC-based plasmid) containing a fluorescence reporter gene GFP (S65T), which was designed to be expressed under the control of a corn ubiquitin promoter and the first intron. The terminator of a nopaline synthase (NOS) gene was added as a terminator.

First, 30 mg of each of 0.3- to 1.6-μm gold particles was weighed out, and 500 μL of 70% ethanol was added thereto and suspended well using a Vortex mixer. Then, the gold particles were precipitated through centrifugation, and the ethanol was removed. Thereafter, 500 μL of 50% glycerol was added, and a sterile gold particle solution was thus obtained.

A plasmid DNA solution (1 μg/μL) purified using Qiagen Plasmid Midi Kit (Qiagen) was placed into a 1.5-mL tube at 5 μg per 750 μg of the gold particles. The sterile gold particle-containing solution was thoroughly suspended using an ultrasonic generator (ultrasonic washer UW-25 manufactured by Taga Electric Co., Ltd.) before use, and placed into the above-mentioned tube in an appropriate amount and stirred with pipetting. Next, 25 μL of 2.5 M $CaCl_2$ (Nacalai Tesque) and 10 μL of 0.1 M Spermidine (Nacalai Tesque) per 750 μg of the gold particles were added to the above-mentioned tube. Immediately after mixing, the resultant mixture was vigorously suspended for 5 minutes using a Vortex mixer. The mixture was left to stand at room temperature for 10 minutes, and was then centrifuged at 9,100×g for 2 seconds. The supernatant was removed, and the precipitation was washed with 70% ethanol and then 99.5% ethanol. Lastly the supernatant was removed, and 24 μL of 99.5% ethanol was added thereto and suspended well. In a clean bench, 6 μL of the suspension was poured to the center of a macrocarrier, and the macrocarrier was then air-dried.

The particle bombardment was performed with Biolistic (registered trademark) PDS-1000/He Particle Delivery System (BIO-RAD). Bombardment pressure was set to about 94.9 kgf/cm² (1,350 psi), and the distance to a target tissue was set to 5 cm (for particles with a diameter of 0.6 μm or more) or 3.5 cm (for particles with a diameter of less than 0.6 μm). The samples were bombarded with the particles at 4 shots per dish. After bombardment, the samples were left to stand overnight in a dark place at 22° C.

(4) Study of Transient Expression Efficiency of GFP Protein

The transfer efficiency of the GFP gene in the shoot apex was calculated through observing GFP fluorescence (excitation: 470/40, absorption: 525/50) in the shoot apex under a stereoscopic fluorescence microscope (MZFL III manufactured by Leica) (FIG. 1). Out of the fully mature embryos subjected to the transformation process, that having 5 or more spots of GFP fluorescence observed in the shoot apex tissue was taken as a transgenic individual, and the gene transfer efficiency was calculated (number of transgenic individuals/number of processed fully mature embryos× 100). As a result, the gene transfer efficiencies in the shoot apex in the cases of the gold particles with diameters of 0.8 μm, 0.6 μm, and 0.3 μm were higher than those in the cases the gold particles with diameters of 1.6 μm and 1.0 μm (Table 1). In particular, when the gold particles with a diameter of 0.6 μm were used, the gene transfer efficiency in the shoot apex was 72.7%, which was the highest compared with those in the cases of the gold particles with different diameters (Table 1). Also, as described later, the gene transfer efficiency in the case of the gold particles with a diameter of 0.6 μm was higher than that in the case of the gold particles with a diameter of 1.0 μm.

TABLE 1

| | | Gold particles per shot (μg) | | |
|---|---|---|---|---|
| | | 187.5 | 375 | 562.5 |
| Gold particle diameter (μm) | 1.6 | 0.0% | 0.0% | 0.0% |
| | 1.0 | 6.7% | 6.7% | 10.0% |
| | 0.8 | 50.0% | 30.0% | 33.3% |
| | 0.6 | 73.3% | 33.3% | 40.0% |
| | 0.3 | 20.0% | 43.4% | 36.7% |

2. Study of $T_0$ Generation Plant Using Genomic PCR as Index (1) Preparation of Fully Mature Seed of Wheat This was performed in accordance with the method described in Example 1-1-(1).

(2) Exposure of Shoot Apex in Embryo of Fully Mature Seed

This was performed in accordance with the method described in Example 1-1-(2).

(3) Gene Introduction

This was performed in accordance with the method described in Example 1-1-(3), proviso that two types of gold particles, namely those with diameters of 0.6 μm and 1.0 μm, were used.

(4) Growth of Individual Subjected to Transformation Process

An individual that had been subjected to the transformation process was left to stand overnight, and was transferred to a disposable container for plant cell culture (Sigma) in which an MS-maltose medium was placed, and was grown in a long-day condition (22° C., day length of 16 hours). After grown for 3 to 4 weeks, the individual was transferred to a pot in which seedling compost for gardening was placed at a time point when the second and third leaves were observed. Thereafter, the individual was grown in a long-day condition in a climatic chamber (24° C., day length of 16 hours, humidity of 50 to 70%) until the fourth to the sixth leaves were out.

(5) Presence or Absence of Transgene in Leaf of to Plant

In the obtained plant body the presence or absence of the GFP gene, which is a fluorescence reporter gene, was examined using a PCR method. A genomic DNA was extracted from the fourth to sixth leaves (50 mg) using a benzyl chloride method, and PCR reaction was performed using the genomic DNA as a template with primers produced based on the sequences specific to the GFP gene.
The sequence of the primer: ACGGCCACAAG-TTCAGCGT (SEQ ID NO: 1)
The sequence of the primer: ACCATGTGATCGCGCTTCT (SEQ ID NO: 2)

A PCR reaction mixture was prepared by mixing 20 ng of the genomic DNA, 0.25 U of ExTaqHS (registered trademark, TaKaRa), 1.5 µL of accompanying 10× buffer 2 mM dNTPs, and the pair of primers (each 2.5 pmol) with sterile distilled water such that the total volume was 15 µl.

In the PCR reaction, the PCR reaction mixture was treated at 95° C. for 3 minutes, and subjected to 33 cycles of reaction of 95° C. for 30 seconds, 60° C. for 30 seconds, and 72° C. for 1 minute using TaKaRa PCR Thermal Cycler Dice (registered trademark). After the PCR reaction, electrophoresis was performed on 1.0% agarose gel, and the PCR product was detected through ethidium bromide staining. The individual in which an expected 601-bp GFP gene fragment was detected was determined as a transgenic individual.

Regarding the two types of gold particles used for the gene introduction, namely those with diameters of 1.0 µm and 0.6 µm, the number of the transgenic individuals was determined, and used to calculate the gene transfer efficiency with respect to the number of the fully mature embryos subjected to the gene introduction process (number of transgenic individuals/number of processed fully mature embryos×100).

As a result, when the gold particles with a diameter of 1.0 µm were used, the transgene was not detected (Table 2). On the other hand, when the gold particles with a diameter of 0.6 µm were used, three individuals were detected as the transgene-detected individuals ($T_0$ generation) (the gene transfer efficiency of 1.4%) (Table 2). Therefore, it was found that the gene transfer efficiency was enhanced by use of the gold particles with a diameter of 0.6 µm, which had high transient expression efficiency in Example 1-1-(4), compared with the gold particles with a diameter of 1.0 µm.

TABLE 2

| Gold particle diameter (µm) | Individuals subjected to transformation | Transgene-detected Individuals ($T_0$ generation) | Gene transfer efficiency ($T_0$ generation) |
|---|---|---|---|
| 1.0 | 499 | 0 | 0 |
| 0.6 | 222 | 3 | 1.4% |

Example 2: Investigation of Gas Pressure Optimum for Gene Introduction

In order to determine a suitable gas pressure, the presence or absence of GFP fluorescence in a shoot apex that had been subjected to a gene introduction process and the presence or absence of a transgene in a current generation ($T_0$ generation) were examined.

1. Study Using Transient Expression System of GFP Fluorescent Protein as Index (1) Preparation of Fully Mature Seed of Wheat This was performed in accordance with the method described in Example 1-1-(1).

(2) Exposure of Shoot Apex in Embryo of Fully Mature Seed

This was performed in accordance with the method described in Example 1-1-(2).

(3) Gene Introduction

This was performed in accordance with the method described in Example 1-1-(3), proviso that the gold particles with a diameter of 0.6 µm were used, and the gas pressure was set to 1,100 psi or 1,350 psi.

(4) Study of Transient Expression Efficiency of GFP Protein

This was performed in accordance with the method described in Example 1-1-(4). As a result, the gene transfer efficiency as described in Example 1-1-(4) was 74.2% at a gas pressure of 1,350 psi, which was higher than 13.3% at a gas pressure of 1,100 psi (Table 3). Also, as described later the gene transfer efficiency in the $T_0$ generation was higher at a gas pressure of 1,350 psi than at a gas pressure of 1,100 psi.

TABLE 3

| Gold particle diameter (µm) | Gas pressure (psi) | No. of Individuals subjected to transformation | No. (%) of individuals expressing GFP in shoot apex | No. (%) of $T_0$ generation transgenic individuals |
|---|---|---|---|---|
| 0.6 | 1,100 | 120 | 16 (13.3) | 1 (0.8) |
|  | 1,350 | 120 | 89 (74.2) | 5 (4.2) |

2. Study of $T_0$ Generation Plant Using Genomic PCR as Index (1) Growth of Individual Subjected to Transformation Process This was performed in accordance with the method described in Example 1-2-(4).

(2) Presence or Absence of Transgene in Leaf of $T_0$ Plant

This was performed in accordance with the method described in Example 1-2-(5). As a result, the gene transfer efficiency as described in Example 1-2-(5) was 4.2% at a gas pressure of 1,350 psi, which was higher than 0.8% at a gas pressure of 1,100 psi (Table 3). Therefore, it was found that the gene transfer efficiency was enhanced by use of a gas pressure of 1,350 psi with which a high efficiency of transient expression of a GFP protein was obtained in Example 2-1-(4), compared with a gas pressure of 1,100 psi.

Example 3: Investigation of Water Absorption Period Optimum for Gene Introduction In order to determine a suitable water absorption period, the presence or absence of GFP fluorescence in a shoot apex that had been subjected to a gene introduction process and the presence or absence of a transgene in a current generation ($T_0$ generation) and a next generation ($T_1$ generation) were examined.

1. Preparation of Fully Mature Embryo and Operation of Gene Introduction (1) Preparation of Fully Mature Seed of Wheat Fully mature seeds of wheat (*Tritcum aestivum* cv. Fielder) were immersed in Haiter (with a hypochlorous acid concentration of 6%), shaken at room temperature for 20 minutes, and washed with sterile water in a clean bench. After having been washed, the seeds were placed on Kimtowel or filter paper moistened with sterile water, and incubated at 4° C. for 2 days. Thereafter, the seeds were incubated at 22° C. for 6 to 12 hours or 12 to 18 hours, and then used in the following experiments. The length of a seminal root was evaluated by measuring the length of a radicle after cutting open a coleorhiza.

(2) Exposure of Shoot Apex in Embryo of Fully Mature Seed

This was performed in accordance with the method described in Example 1-1-(2).

(3) Gene Introduction

This was performed in accordance with the method described in Example 1-1-(3), proviso that the gold particles with a diameter of 0.6 μm were used.

2. Study of to and $T_1$ Generation Plants Using Genomic PCR as Index (1) Growth of Individual Subjected to Transformation Process The individual in which transient GFP fluorescence was observed in the shoot apex in Example 3-1-(3) was grown in accordance with the method described in Example 1-(2)-4.

(2) Presence or Absence of Transgene in Leaf of $T_0$ Plant

Figure 2:
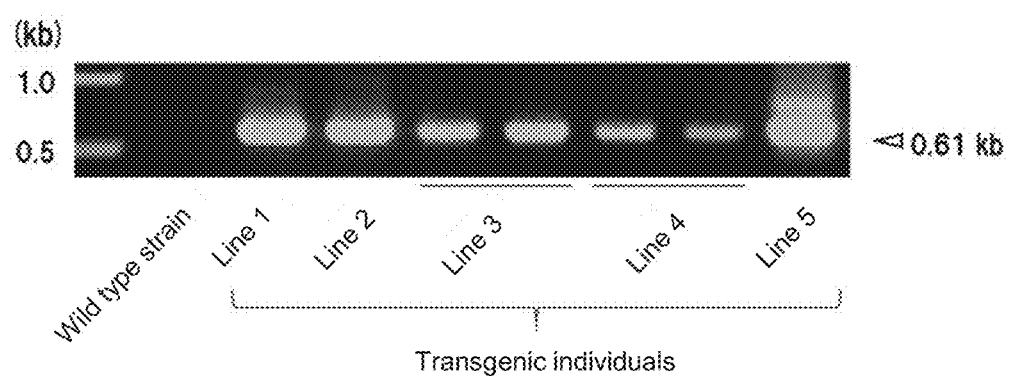
FIG. 2 is a diagram showing the results of the confirmation of the transgene in $T_1$ generation transformants in Example 2 according to one or more embodiments of the present invention, by a genomic PCR.

This was performed in accordance with the method described in Example 1-2-(5). For the fully mature embryos subjected to the transformation process after the respective water absorption periods, the number of the transgene-detected individuals ($T_0$ generation) was determined and used to calculate the gene transfer efficiency with respect to the number of the fully mature embryos subjected to the gene introduction process (number of transgenic individuals/number of processed fully mature embryos×100). As a result, when the fully mature seeds after the 6- to 12-hour water absorption period and after the 12- to 18-hour water absorption period were used in the experiment, the gene transfer efficiencies were 3.1% and 1.3%, respectively (Table 3), and the gene transfer efficiency was particularly high with the fully mature embryo after the 6- to 12-hour water absorption period (Table 4).

ments, the gene transfer efficiencies were 3.1% (lines 1 and 2 in FIG. 2, Table 3) and 0.7% (lines 3 to 5 in FIG. 2, Table 3), respectively and the gene transfer efficiency was particularly high with the fully mature embryo after the 6- to 12-hour water absorption period. It was determined from these results that the fully mature seed at the early stage of a water absorption period (between about 6 hours later and 18 hours later; a seminal root having a length of 1.0 mm or less) is suitable for the gene introduction, and the fully mature seed after 6- to 12-hour water adsorption period may be preferable.

Figure 3:
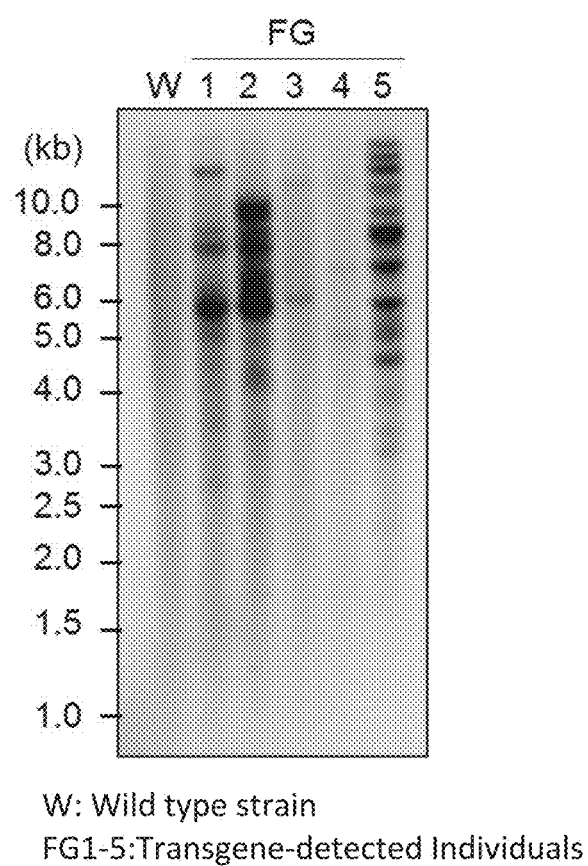
FIG. 3 is a photograph showing the result of Southern analysis for transgenic individuals (Example 3).

Regarding the five lines of the transgene-detected individuals ($T_1$ generation) shown in Table 4, the insertion of the GFP gene into the genomic DNA was confirmed through Southern blotting analysis with a probe of the GFP gene region (FIG. 3).

Example 4: Confirmation of Gene Expression in $T_1$ Generation

In the transformed wheat produced using the gene introduction method, the presence or absence of the expression of the transgene (GFP gene) was examined.

1. Observation of GFP Fluorescence in $T_1$ Seed

Figure 4A:
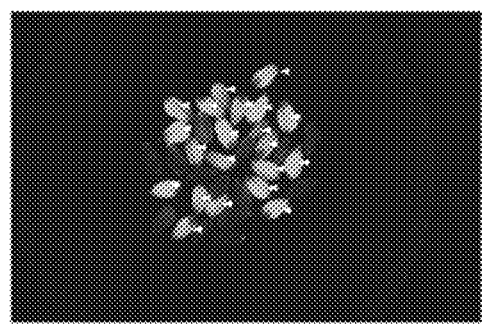
FIG. 4A is a photograph showing the whole of $T_1$ generation seeds in Example 4 according to one or more embodiments of the present invention, observed with GFP fluorescence.
Figure 4B:
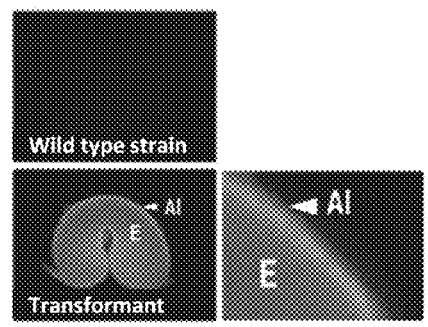
FIG. 4B is a photograph showing a half-cut of $T_1$ generation seed in Example 4 according to one or more embodiments of the present invention, observed with GFP fluorescence.

The $T_1$ seeds obtained in Example 3-2-(3) were placed on a sterile dish, and were observed for GFP fluorescence in the $T_1$ seeds under LAS 3000 (FujiFilm) (filter: 510DF10). As a result, GFP fluorescence was observed in the seeds (FIG. 4A). Next, the seed in which GFP fluorescence was observed was cut in half, and was observed for GFP fluorescence (excitation: 470/40, absorption: 525/50) of the endosperm under a stereoscopic fluorescence microscope (MZFL III manufactured by Leica). As a result, GFP fluorescence was observed in the endosperm (E), and GFP fluorescence was intensively observed in the aleurone layer (Al) (FIG. 4B).

2. Analysis of GFP Fluorescent Protein Expression in $T_1$ Generation Young Leaf Young leaves of the $T_1$ generation plant grown in Example 3-2-(3) were sampled, and were observed for GFP fluorescence (excitation: 470/40, absorption: 525/50) in the

TABLE 4

| Water absorption period (hr) | Seed root length (mm) | No. of processed individuals | Transgene-detected Individuals ($T_0$ generation) | Gene transfer efficiency ($T_0$ generation) | Transgene-detected Individuals ($T_1$ generation) | Gene transfer efficiency ($T_1$ generation) |
|---|---|---|---|---|---|---|
| 6-12 | ≤1.0 | 64 | 2 | 3.1% | 2 | 3.1% |
| 12-18 |  | 452 | 6 | 1.3% | 3 | 0.7% |

(3) Presence or Absence of Transgene in Leaf of $T_1$ Plant

Figure 4C:
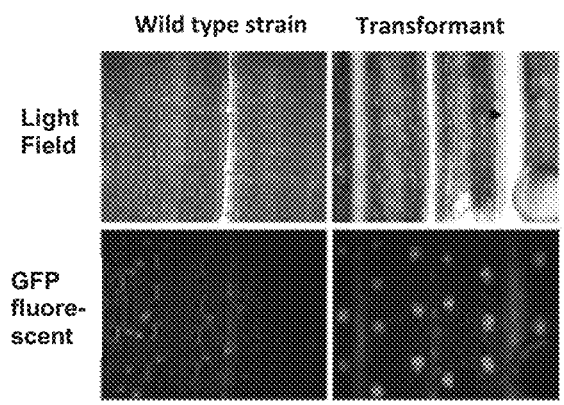
FIG. 4C is a photograph showing a $T_1$ generation young leaf in Example 4 according to one or more embodiments of the present invention, observed with GFP fluorescence.

The transgene-detected individual in (2) above was grown, and $T_1$ seeds were obtained. About ten to twenty $T_1$ seeds were sowed and grown, and the first leaf (50 mg) was sampled. Genomic PCR and electrophoresis were performed in accordance with Example 1-(2)-5. The fully mature embryos after the respective water absorption periods were subjected to the transformation process, and the number of the transgene-detected individuals ($T_1$ generation) was determined and used to calculate the gene transfer efficiency with respect to the number of the fully mature embryos subjected to the gene introduction process (number of transgenic individuals/number of processed fully mature embryos×100). As a result, when the fully mature seeds after the 6- to 12-hour water absorption period and after the 12- to 18-hour water absorption period were used in the experileaves under a stereoscopic fluorescence microscope (MZFL III manufactured by Leica). As a result, as shown in FIG. 4C, GFP fluorescence was observed in stomatal cells of the leaves in the genomic PCR-positive individual (transformant).

Next, total proteins were extracted from adult leaves of a wild-type strain and a transformant (transgenic individual) to detect a GFP fluorescent protein through Western blotting. First, 1 g of the adult leaf was frozen using liquid nitrogen and pulverized, and then was suspended in a protein extraction buffer (0.25 M sorbitol, 50 mM Tris/acetate, pH 7.5, 1 mM EDTA, 2 mM DTT, 1% PVP, 10 μM PMSF). The extract was centrifuged (1,100×g, 15 minutes, 4° C.), and the supernatant was further centrifuged (12,800×g, 15 minutes, 4° C.). The supernatant obtained after this centrifugation was taken as a total protein fraction. Then, 20 μg of the total protein fraction was subjected to electrophoresis with 12.5% SDS-polyacrylamide gel, and transferred to a nitrocellulose membrane using a semidry method. The membrane was shaken in a blocking buffer (5% (w/v) Skim Milk Powder in TTBS (10 mM Tris-HCl, 150 mM NaCl, 0.05% Tween-20, pH 7.5)) for 1 hour. After washing of the membrane with TTBS for 5 minutes was performed three times, a primary antibody was reacted with the membrane for 1 hour. After washing of the membrane with TTBS for 5 minutes was performed three times, a secondary antibody was reacted with the membrane for 1 hour. After washing of the membrane with TTBS for 5 minutes was performed three times, detection was performed in accordance with the instruction manual of Amersham ECL Western blotting analysis system (GE Healthcare). Mouse $IgG_1$ K-derived GFP antibody (ROCHE) was used (2000-fold dilution) as the primary antibody and peroxidase-labeled anti-mouse IgG antibody included in the above-mentioned kit was used (5000-fold dilution) as the secondary antibody.

Figure 4D:
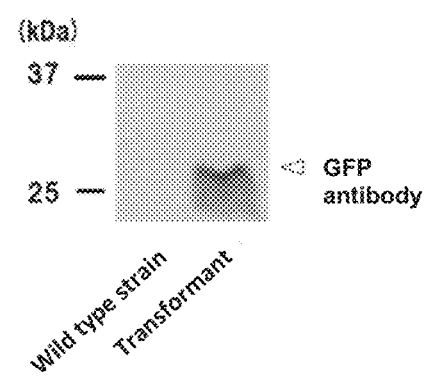
FIG. 4D is a photograph showing Western blotting for detecting GFP protein in a $T_1$ generation adult leaf in Example 4 according to one or more embodiments of the present invention.

As a result of Western blotting analysis, a signal was observed at near 27 kDa of an estimated molecular weight of the GFP protein in the transformant, but no signals were detected in the wild-type strain (FIG. 4D). It was confirmed from these results that the transgene was normally expressed in the transformed plant produced using the above-described gene introduction method.

Transformants of barley corn, rice, soybean, potato, and apple can also be obtained using substantially the same method as the method used to obtain a transformant of wheat.

Example 5: Confirmation of Genotypes of $T_1$ Generation Individuals Obtained from Single Line of $T_0$ Generation The transgenic individual ($T_0$ generation) produced using the method is a chimera, which is an individual in which cells having different genetic information coexist. Therefore, Southern blotting analysis was performed in order to examine whether or not a plurality of $T_1$ seeds obtained from a certain single line of transgenic individual ($T_0$ generation) had different genetic information.

$T_1$ seeds were harvested from spikes derived from the main stem and five tillers of an individual of line FG1 at $T_0$ generation obtained in Example 3-2-(3), and a plurality of individuals out of them were sowed. The sowed $T_1$ generation individuals were grown, and the presence or absence of the transgene in the $T_1$ generation individuals was examined in accordance with the method described in Example 3-2-(3). As a result, the transgene was detected in the $T_1$ individuals harvested from the spikes derived from the main stem and tillers other than tiller 2 (Table 5).

TABLE 5

| Source of spikes | No. of $T_1$ seeds harvested from spike | No. of $T_1$ seeds analyzed | Transgenic individuals ($T_0$ generation) |
| --- | --- | --- | --- |
| Main stem | 35 | 31 | 26 |
| Tiller 1 | 25 | 24 | 6 |
| Tiller 2 | 25 | 25 | 0 |
| Tiller 3 | 27 | 27 | 22 |
| Tiller 4 | 23 | 23 | 22 |
| Tiller 5 | 7 | 7 | 5 |

Figure 5A:
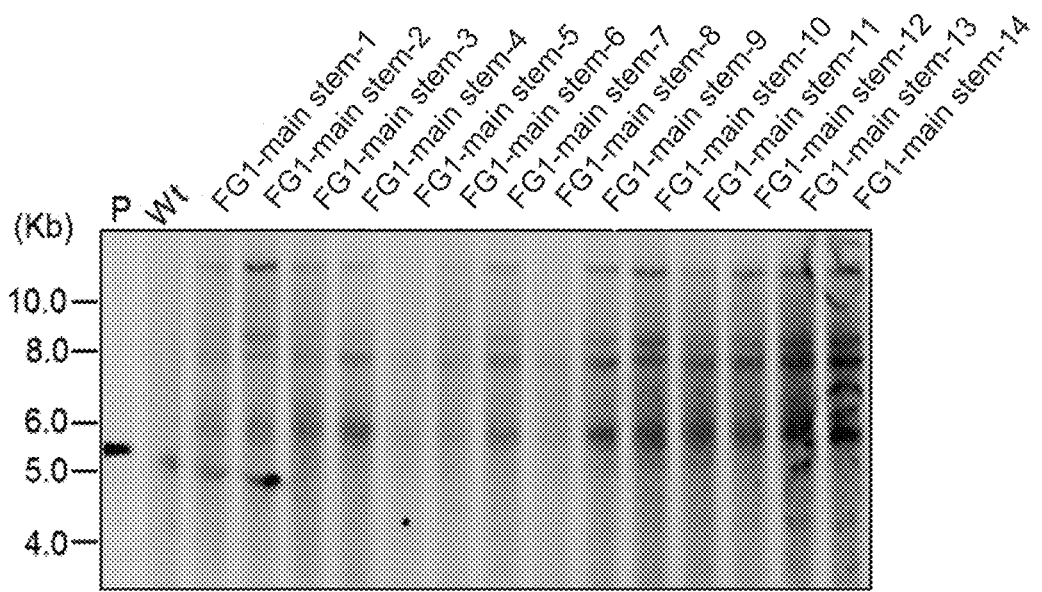
FIG. 5A is a photograph showing the results of Southern analysis of genomic DNAs obtained from young leaves of $T_1$ seeds derived from a main stem.
Figure 5B:
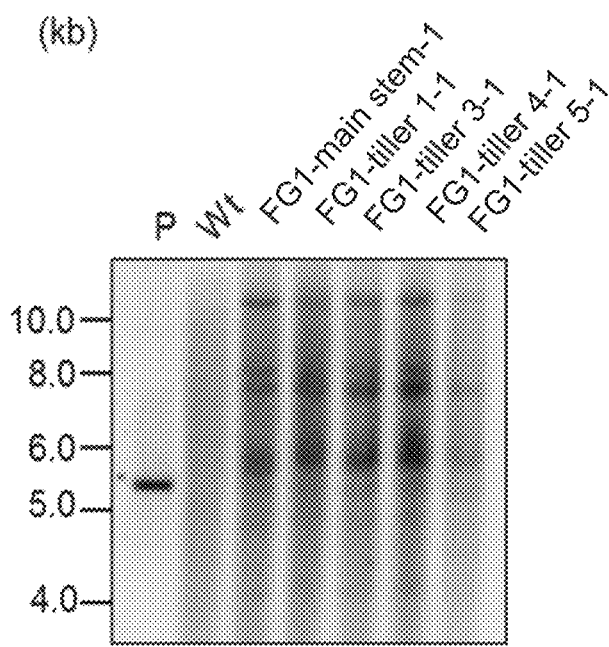
FIG. 5B is a photograph showing the results of Southern analysis of genomic DNAs obtained from young leaves of $T_1$ seeds derived from a main stem and tillers (Example 5).

Next, genomic DNAs obtained from young leaves of fourteen $T_1$ seeds derived from the main stem (FG1-main stem-1 to 14) were treated with HindIII, and Southern blotting analysis was performed with a probe of the GFP gene region. As a result, the same signal pattern was obtained for all the individuals (FIG. 5A). Furthermore, genomic DNAs obtained from young leaves of T seeds derived from the main stem and tillers 1, 3, 4, and 5 (FG1-main stem-1, FG1-tiller 1-1, FG1-tiller 3-1, FG1-tiller 4-1, FG1-tiller 5-1) were treated with HindIII, and Southern blotting analysis was performed as described above. As a result, the same signal pattern was obtained for all the individuals (FIG. 5B). It was found from these results that the plurality of $T_1$ seeds obtained from a certain single line of the transgenic individual ($T_0$ generation) had the same genetic information. This suggests that a very small number of shoot apical stem cells transit to a germ cell line, and it was found that a gene can be introduced into the very small number of shoot apical stem cells by the method.

Example 6: Obtainment of Transformant of Corn

In order to confirm whether or not a transformant of corn can be obtained using the same method as the method used to obtain a transformant of wheat, the presence or absence of GFP fluorescence in a shoot apex that had been subjected to a gene introduction process was examined.

1. Study Using Transient Expression System of GFP Fluorescent Protein as Index (1) Preparation of Fully Mature Seed of Corn Fully mature seeds of corn (Snowdent Ohka) were immersed in Haiter (with a hypochlorous acid concentration of 6%), shaken at room temperature for 20 minutes, and washed with sterile water in a clean bench. After having been washed, the seeds were placed on Kimtowel or filter paper moistened with sterile water, and incubated at 30° C. for about 36 hours, and then used in the following experiments.

(2) Exposure of Shoot Apex in Embryo of Fully Mature Seed

An endosperm and an excess portion of a scutelumn were removed using a sterile knife (or a sterile scalpel) under a stereoscopic microscope. Thereafter, a coleoptile and leaf primordia in the embryonic moiety of each of the above-mentioned germinated seeds were removed using a leading end of a needle (with a diameter of 0.20 mm), and the shoot apex moiety was thus fully exposed. The thus obtained samples were placed on an MS-maltose medium (4.3 g/L MS salt, MS vitamin, 30 g/L maltose, 0.98 g/L MES, 3% PPM (plant preservative mixture, registered trademark; Nacalai Tesque Inc.), 7.0 g/L phytagel, pH 5.8) at 1.0 samples per plate. The above-mentioned plates was prepared at two plates per treatment group.

(3) Gene Introduction

This was performed in accordance with the method described in Example 1-1-(3).

(4) Study of Transient Expression Efficiency of GFP Protein

Figure 6:
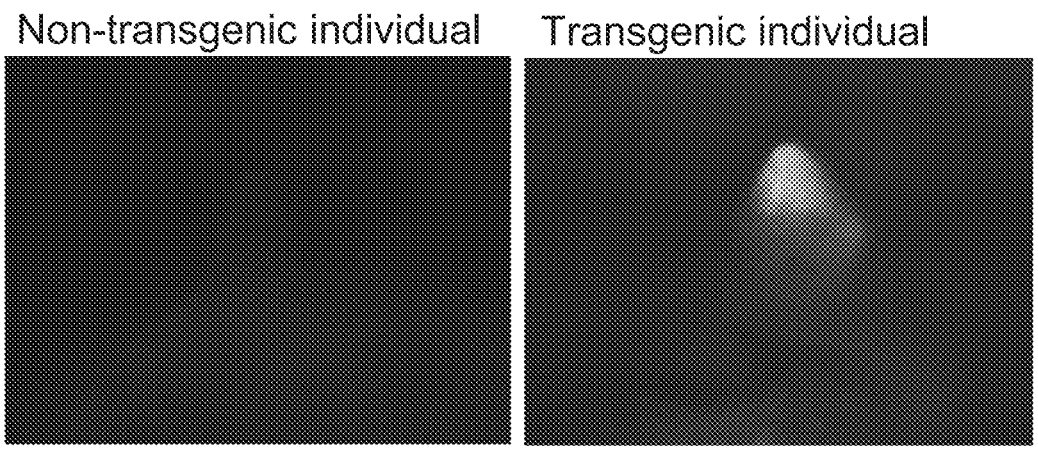
FIG. 6 is a photograph showing a transient expression of GFP in corn (Example 6).

The transfer efficiency of the GFP gene in the shoot apex was calculated by observing GFP fluorescence (excitation: 470/40, absorption: 525/50) absorption: 525/50) in the shoot apex under a stereoscopic fluorescence microscope (MZFL III manufactured by Leica) (FIG. 6). Out of the fully mature embryos subjected to the transformation process, that having 5 or more spots of GFP fluorescence observed in the shoot apex tissue was taken as a transgenic individual, and the gene transfer efficiency was calculated (number of transgenic individuals/number of processed fully mature embryos×100). As a result, the gene transfer efficiencies in the shoot apex in the cases of the gold particles with diameters of 0.8 μm, 0.6 μm, and 0.3 μm were higher than those in the cases of the gold particles with diameters of 1.6 μm and 1.0 μm (Table 6). In particular, when the gold particles with a diameter of 0.6 μm were used, the gene transfer efficiency in the shoot apex was 85%, which was the highest compared with those in the cases of the gold particles with different diameters (Table 6).

TABLE 6

|  | Gold particle diameter (μm) | | | | |
| --- | --- | --- | --- | --- | --- |
|  | 0.3 | 0.6 | 0.8 | 1.0 | 1.6 |
| Gene transfer efficiency | 25.0% | 85.0% | 20.0% | 5.0% | 5.0% |

Example 7: Obtainment of Transformant of Soybean

In order to confirm whether or not a transformant of soybean can be obtained using the same method as the method used to obtain a transformant of wheat, the presence or absence of GFP fluorescence in a shoot apex that had been subjected to a gene introduction process and the subsequently transformant obtaining efficiency were examined.

1. Study Using Transient Expression System of GFP Fluorescent Protein as Index (1) Preparation of Fully Mature Seed of Soybean Fully mature seeds of soybean (Yukihomare) were immersed in Haiter (with a hypochlorous acid concentration of 6%), shaken at room temperature for 3 minutes, and washed with sterile water in a clean bench. After having been washed, the seeds were placed on Kimtowel or filter paper moistened with sterile water, incubated at 23° C. for about 40 hours, and then used in the following experiments.

(2) Exposure of Shoot Apex of Embryo in Fully Mature Seed

The entire cotyledon was cut out using a sterile knife (or a sterile scalpel) under a stereoscopic microscope, and only a hypocotyl was left. Thereafter, a primary leaf and a base of the hypocotyl were removed using a leading end of a needle (with a diameter of 0.20 mm), and the shoot apex moiety was thus fully exposed. The thus obtained samples were placed on a BM medium (4.3 g/L MS salt, MS vitamin, 3% sucrose, 0.50 g/L MES, 3% PPM (plant preservative mixture; Nacalai Tesque Inc.), 6.0 g/L phytagel, pH 5.7) at about 15 samples per plate.

(3) Gene Introduction

This was performed in accordance with the method described in Example 1-1-(3), proviso that a 35S promoter of a cauliflower mosaic virus (CaMV) was used as a promoter.

(4) Study of Transient Expression Efficiency of GFP Protein

Figure 7:
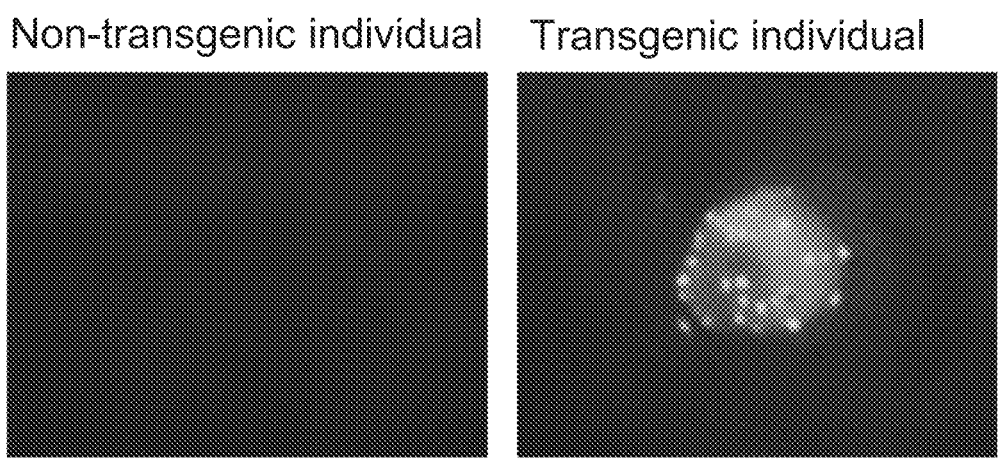
FIG. 7 is a photograph showing a transient expression of GFP in soybean (Example 7).

The transfer efficiency of the GFP gene in the shoot apex was calculated by observing GFP fluorescence (excitation: 470/40, absorption: 525/50) in the shoot apex under a stereoscopic fluorescence microscope (MZFL III manufactured by Leica) (FIG. 7). Out of the fully mature embryo subjected to the transformation process, that having 5 or more spots of GFP fluorescence observed in the shoot apex tissue was taken as a transgenic individual, and the gene transfer efficiency was calculated (number of transgenic individuals/number of processed fully mature embryos× 100). As a result, the gene transfer efficiency in the shoot apex in the case of the gold particles with a diameter of 0.6 μm was 85.0%, which was higher than those in the cases of the gold particles with diameters of 1.6 μm and 1.0 μm (Table 7).

TABLE 7

|  | Gold particle diameter (μm) | | |
| --- | --- | --- | --- |
|  | 0.6 | 1.0 | 1.6 |
| Gene transfer efficiency | 85.0% | 30.6% | 4.3% |

2. Study of $T_0$ Generation Plant Using Genomic PCR as Index (1) Growth of Individual Subjected to Transformation Process An individual that had been subjected to the transformation process was left to stand overnight, and was transferred to a disposable container for plant cell culture (Sigma) in which an RM medium (4.3 g/L MS salt, MS vitamin, 3% sucrose, 0.50 g/L MES, 3% PPM (plant preservative mixture; Nacalai Tesque Inc.), 0.3% Gelrite, pH 5.7) was placed, and was grown in an incubator (23° C., day length of 16 hours). The individual was transferred to a cell tray in which seedling compost for gardening was placed at a time point when the growth of a root and the differentiation of the shoot apex into a leaf were observed. Thereafter, the individual was grown in the same incubator until the second leaf was out.

(2) Presence or Absence of Transgene in Leaf of $T_0$ Plant

In the obtained plant body the presence or absence of the GFP gene, which is a fluorescence reporter gene was examined using a PCR method. A genomic DNA was extracted from the second leaf (50 mg) using a benzyl chloride method, and PCR reaction was performed using the genomic DNA as a template with primers produced based on the sequences specific to the GFP gene.

```
The sequence of the primer:
                                    (SEQ ID NO: 1)
ACGGCCACAAGTTCAGCGT The sequence of the primer:
                                    (SEQ ID NO: 2)
ACCATGTGATCGCGCTTCT
```

A PCR reaction mixture was prepared by mixing 20 ng of the genomic DNA, 0.25 U of ExTaqHS (TaKaRa), 1.5 μL of accompanying 10× buffer, 2 mM dNTPs, and the pair of primers (each 2.5 pmol) with sterile distilled water such that the total volume was 15 μl.

In the PCR reaction, the PCR reaction mixture was treated at 95° C. for 3 minutes, and subjected to 32 cycles of reaction of 95° C. for 30 seconds, 60° C. for 30 seconds, and 72° C. for 1 minute using TaKaRa PCR Thermal Cycler Dice. After the PCR reaction, electrophoresis was performed on 1.0% agarose gel, and the PCR product was detected through ethidium bromide staining and irradiation with ultraviolet rays. The individual in which an expected 601-bp GFP gene fragment was detected was determined as a transgenic individual.

Regarding the two types of gold particles with diameters of 1.0 μm and 0.6 μm, used for the gene introduction, the number of the transgenic individuals was determined and used to calculate the gene transfer efficiency with respect to the number of the fully mature embryos subjected to the gene introduction process (number of transgenic individuals/number of processed fully mature embryos×100).

As a result, when the gold particles with a diameter of 0.6 μm were used, the transgene-detected individuals ($T_0$ generation) were 63 individuals out of 470 processed fully mature embryos (the gene transfer efficiency of 13.4%). Therefore, it was found that the transgenic individuals of soybean could be obtained with high efficiency by use of the gold particles with a diameter of 0.6 pin, which had high transient expression efficiency in Example 7-1-(4).

Example 8: Obtainment of Transformant of Barley

Figure 8:
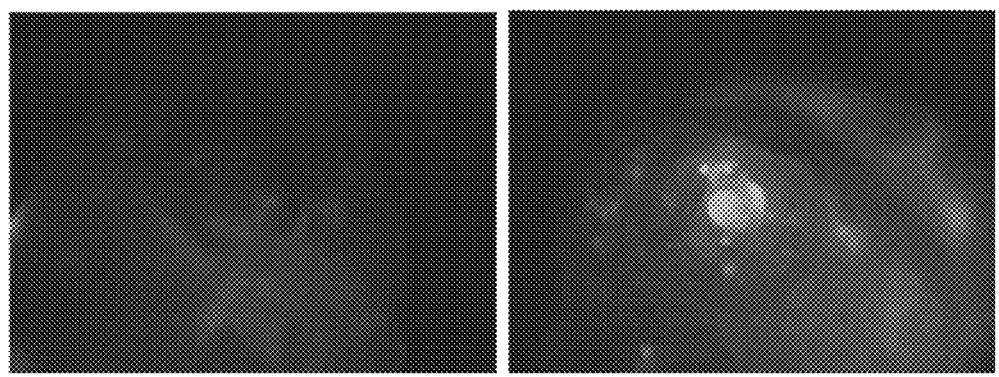
FIG. 8 is a photograph showing a transient expression of GFP in barley (Example 8).

In order to confirm whether or not a transformant of barley can be obtained using the same method as the method used to obtain a transformant of wheat, the presence or absence of GFP fluorescence in a shoot apex that had been subjected to a gene introduction process was examined.
1. Study Using Transient Expression System of GFP Fluorescent Protein as Index
(1) Preparation of Fully Mature Seed of Barley
Fully mature seeds of barley (Wasedori-nijo) were immersed in Haiter (with a hypochlorous acid concentration of 6%), shaken at room temperature for 20 minutes, and washed with sterile water in a clean bench. Ater having been washed, the seeds were placed on Kimtowel or filter paper moistened with sterile water, and incubated at 4° C. for 2 days. Thereafter, the seeds were incubated at 22° C. for 6 to 12 hours and then used in the following experiments.
(2) Exposure of Shoot Apex in Embryo of Fully Mature Seed
An endosperm and an excess portion of a scutellum were removed using a sterile scalpel under a stereoscopic microscope. Thereafter, a coleoptile and leaf primordia in the embryonic moiety of each of the above-mentioned germinated seeds were removed using a leading end of a needle (with a diameter of 0.20 mm), and the shoot apex moiety was thus fully exposed. The thus obtained samples were placed on an MS-maltose medium (4.3 g/L MS salt, MS vitamin, 30 g/L maltose, 0.98 g/L MES, 3% PPM (plant preservative mixture, registered trademark; Nacalai Tesque Inc.), 7.0 g/L phytagel, pH 5.8) at 30 samples per plate.
(3) Gene Introduction
This was performed in accordance with the method described in Example 1-1-(3).
(4) Study of Transient Expression Efficiency of GFP Protein
This was performed in accordance with the method described in Example 1-1-(4). As a result, the gene transfer efficiencies in the shoot apex in the cases of the gold particles with diameters of 0.8 μm, 0.6 μm, and 0.3 μm were higher than those in the cases of the gold particles with diameters of 1.6 μm and 1.0 μm (Table 9). In particular, when the gold particles with a diameter of 0.3 μm were used, the gene transfer efficiency in the shoot apex was 80.0%, which was the highest compared with those in the cases of the gold particles with different diameters (FIG. 8, Table 8).

TABLE 8

| | Gold particle diameter (μm) | | | | |
|---|---|---|---|---|---|
| | 0.3 | 0.6 | 0.8 | 1.0 | 1.6 |
| Gene transfer efficiency | 80.0% | 73.3% | 73.3% | 16.7% | 6.7% |

Example 9: Obtainment of Transformant of Potato

Figure 9:
FIG. 9 is a photograph showing a transient expression of GFP in potato (Example 9).

In order to confirm whether or not a transformant of potato can be obtained using the same method as the method used to obtain a transformant of wheat, the presence or absence of GFP fluorescence in a shoot apex that had been subjected to a gene introduction process was examined.
1. Preparation of Potato
A seed potato (Danshaku) was sterilized using Haiter (with a hypochlorous acid concentration of 1%), washed with water dried, and was incubated under a fluorescent lamp at 22° C. for 1 to 2 weeks so as to sprout.
2. Exposure of Shoot Apex
Leaf primordia were removed from a sprout using a sterile scalpel and a leading end of a needle (with a diameter of 0.20 mm) under a stereoscopic microscope, and the shoot apex moiety was thus fully exposed. The thus obtained samples were placed on an MS medium (4.3 g/L MS salt, MS vitamin, 30 g/L sucrose, 0.98 g/L MES, 3% PPM (plant preservative mixture, registered trademark; Nacalai Tesque Inc.), 7.0 g/L phytagel, pH 5.8) at 40 samples per plate.
3. Gene Introduction
This was performed in accordance with the method described in Example 1-1-(3), proviso that pUC18-35S-GFP was used as an introduction vector.
4. Study of Transient Expression Efficiency of GFP Protein
This was performed in accordance with the method described in Example 1-1-(4). As a result, GFP fluorescence could be observed in the shoot apex in the case where the gold particles with a diameter of 0.6 μm were used. (FIG. 9).

Example 10: Obtainment of Transformant of Rice

A transformant of rice can also be obtained using substantially the same method as the method used to obtain a transformant of wheat.
1. Preparation of Fully Mature Seed of Rice
After threshed fully mature seeds of rice (strain: Nihonbare) are sterilized and washed in accordance with the method described in Example 1-1-(1), the seeds are placed on Kimtowel or filter paper moistened with sterile water, incubated at 25° C. for about 24 to 48 hours, and then used in the following experiments.
2. Exposure of Shoot Apex in Embryo of Fully Mature Seed
A shoot apex of an embryo in the fully mature seed is fully exposed in accordance with the method described in Example 1-1-(2). The fully mature embryos including an exposed shoot apex are placed on an MS-maltose medium at about thirty embryos per plate.
3. Gene Introduction
The gene introduction into the shoot apex of the fully mature embryo of rice is performed in accordance with the method described in Example 1-1-(3).
4. Selection Using Transient Expression of GFP Protein as Index
Out of the individuals subjected to the transformation process using the gold particles with a diameter of 0.6 μm, an individual in which GFP fluorescence is observed in the shoot apex tissue is selected in accordance with the method described in Example 1-1-(4).
5. Growth of Individual Subjected to Transformation Process
The individual subjected to the transformation process is grown in accordance with the method described in Example 1-2-(4).

6. Confirmation of Transgene in Leaf of $T_0$ Plant

A transgene-detected individual is obtained in accordance with the method described in Example 1-2-(5). The obtained individual is grown, and seeds of next generation are obtained, thus making it possible to produce a stable transformant.

Example 11: Obtainment of Transformant of Apple

A transformant of apple can also be obtained using substantially the same method as the method used to obtain a transformant of wheat.

1. Preparation of Shoot Apex of Apple

The preparation of a shoot apex of apple (strain: Jonagold) is performed according to the induction conditions for shoot apex culture described in Plant Tissue Culture Letters, 9(2), 69-73 (1992).

2. Exposure of Shoot Apex

The shoot apexes prepared using the method in 1 are placed on an MS-maltose medium (4.3 g/L MS salt, MS vitamin, 380 g/L maltose, 0.98 g/L MES, 3% PPM (plant preservative mixture, registered trademark; Nacalai Tesque Inc.), 7.0 g/L phytagel, pH 5.8) at about thirty apexes per plate.

3. Gene Introduction

This is performed in accordance with the method described in Example 1-1-(1), proviso that a 35S promoter of a cauliflower mosaic virus (CaMV) is used as a promoter.

4. Selection Using Transient Expression of GFP Protein as Index

Out of the individuals subjected to the transformation process using the gold particles with a diameter of 0.6 μm, an individual in which GFP fluorescence is observed in the shoot apex tissue is selected in accordance with the method described in Example 1-1-(4).

5. Growth of Individual Subjected to Transformation Process

The individual subjected to the transformation process is grown in accordance with the method described in Example 1-2-(4).

6. Confirmation of Transgene in Leaf of $T_0$ Plant

An transgene-detected individual is obtained in accordance with the method described in Example 1-2-(5). The obtained individual is grown, and seeds of next generation are obtained, thus making it possible to produce a stable transformant.

Example 12: Target Mutagenesis Using Gene Introduction Method

In order to evaluate whether or not the gene introduction method can be used to edit the wheat genome, mutagenesis of a target sequence was attempted with RNA inducible CRISPR/Cas9. It was found from the results of Example 1-1-(4) that gold particles with a diameter of 0.3 μm or more and 0.9 μm or less may be preferably used to produce a stable transformant using the gene introduction method. However, there is no limitation to the above-mentioned particle diameter as it is only necessary to express transiently a nuclease or the like in the nucleus or an organelle of a plant cell for the production of a genome-edited individual. Accordingly a range of the diameter of gold particles was evaluated for allowing a genome editing of wheat using the gene introduction method.

1. Confirmation of Target Mutagenesis Using GFP Fluorescence as Index (1) Preparation of Fully Mature Seed of Wheat Fully mature seeds of wheat (*Triticum aestivum* cv. Fielder) were immersed in Haiter (with a hypochlorous acid concentration of 6%), shaken at room temperature for 20 minutes, and washed with sterile water in a clean bench. After having been washed, the seeds were placed on Kimtowel or filter paper moistened with sterile water and incubated at 4° C. for 2 days for the purpose of breaking dormancy Thereafter, the seeds were incubated at 22° C. for about 12 hours and then used in the following experiments.

(2) Exposure of Shoot Apex in Embryo of Fully Mature Seed

This was performed in accordance with the method described in Example 1-1-(2).

(3) Gene Introduction

The gene introduction into the shoot apex of the fully mature embryo of wheat was performed using a particle bombardment method as described below.

In this example, it was used that a target plasmid DNA (pUC-based plasmid) in which a 20-bp partial sequence (CCGTCACGCAGGACCCAATCTCC: SEQ ID NO: 3) within a TaMLO gene was inserted as a target sequence at a position directly behind the initiation codon of a fluorescence reporter gene (GFP), which was designed to be expressed under the control of a ubiquitin promoter of corn and the first intron. The terminator of a nopaline synthase (NOS) gene was added as a terminator. The vector and a gRNA/Cas9-integrated plasmid is introduced together, so that the TaMLO gene target sequence is cleaved by Cas9 and two-base deletion or one-base insertion is induced in the process of repairing. As a result, translational frameshifting occurred, leading to the recovery of the reading frame for codons of the GFP gene and the expression of an active GFP protein.

In the integrated plasmid (pUC-based plasmid), a gRNA was designed to be expressed under the control of a U6 promoter derived from wheat. Also, the Cas9 gene was designed to be expressed under the control of a ubiquitin promoter of corn and the first intron. The terminator of a nopaline synthase (NOS) gene was added as a terminator.

The gold particles were prepared and introduced in accordance with the method described in Example 2-1-(3), proviso that the target plasmid DNA solution and the gRNA/Cas9-integrated plasmid were added at 2.5 μg and 7.5 μg per 750 μg of the gold particles, respectively. The amount of the gold particles was set to 375 μg per shot in the case of the gold particles with a diameter of 0.3 μm, and the amount of the gold particles was set to 187.5 μg per shot in the cases of the gold particles with different diameters.

(4) Confirmation of GFP Fluorescence Through TaMLO Gene Sequence Cleavage

Figure 10:
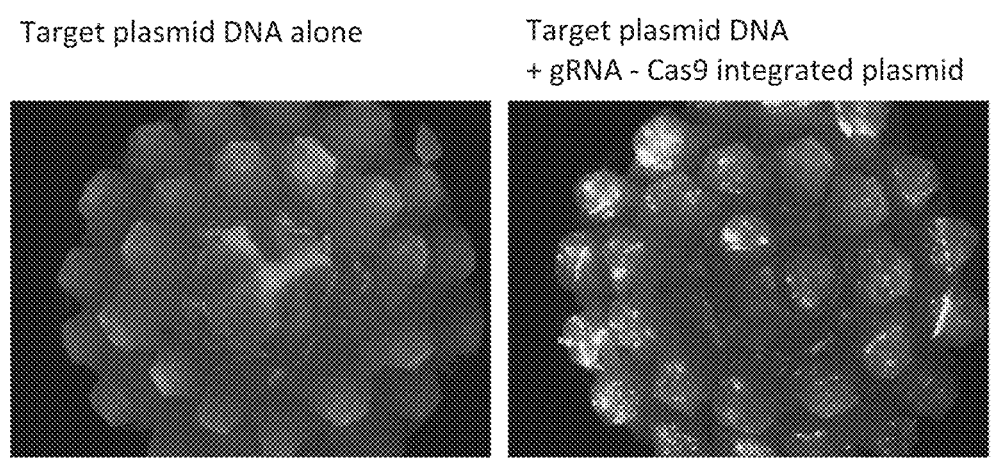
FIG. 10 shows a target gene introduced individual (Example 12).

The presence or absence of the cleavage of the TaMLO gene target sequence was examined by observing GFP fluorescence (excitation: 470/40, absorption: 525/50) in the shoot apex under a stereoscopic fluorescence microscope (MZFL III, Leica). Out of the fully mature embryos subjected to the gene introduction process, that having 1 or more spots of GFP fluorescence observed in the shoot apex tissue was taken as a target sequence-cleaved individual, and target sequence cleavage efficiency was calculated (number of target sequence-cleaved individuals/number of processed fully mature embryos×100). The experiment was performed twice. Table 11 shows an average value of the target sequence cleavage efficiency. As a result, when the target plasmid DNA and the gRNA/Cas9-integrated plasmid were introduced together, GFP fluorescence, indicating the cleavage of the target sequence, was observed in the case of the gold particles with diameters of 0.3 μm to 1.0 μm, while not observed in the case of the gold particles with a diameter of 1.6 μm (Table 9). When the gold particles with a diameter of 0.6 μm were used, the efficiency was 23.5%, which was the highest (Table 9, FIG. 10). It was found from these results that the gold particles with a diameter of less than 1.6 μm were suitable to produce a genome-edited individual using the gene introduction method, and the gold particles with diameter of 0.6 μm was preferable.

TABLE 9

| | Gold particle diameter (μm) | | | | |
|---|---|---|---|---|---|
| | 0.3 | 0.6 | 0.8 | 1.0 | 1.6 |
| Target sequence cleavage efficiency | 8.8% | 23.5% | 11.8% | 5.9% | 0.0% |

Example 13: Target Mutagenesis Using Gene Introduction Method ($T_0$ Generation, $T_1$ Generation)

In order to evaluate whether or not the gene introduction method can be used for genome editing of a target gene present in wheat, mutagenesis of a TaQsd1 gene (alanine aminotransferase gene), a TaLOX2 gene (lipoxygenase gene), and a TaGASR7 gene (Snakin/GASA gene) was attempted with the RNA inducible CRISPR/Cas9. A commercial variety "Haruyokoi" was used for the mutagenesis of the TaQsd1 gene, and "Bobwhite" was used for the mutagenesis of the other genes.

1. Confirmation of Target Gene Mutagenesis a Week after Gene Introduction (1) Preparation of Fully Mature Seed of Wheat This was performed in accordance with the method described in Example 1-1-(1), proviso that fully mature seeds of wheat (*Triticum aestivum* cv. Bobwhite, *Triticum aestivum* cv. Haruyokoi) were used.

(2) Exposure of Shoot Apex in Embryo of Fully Mature Seed

This was performed in accordance with the method described in Example 1-1-(2).

(3) Gene Introduction

The gene introduction into the shoot apex of the fully mature embryo of wheat was performed using a particle bombardment method as described below.

In this example, in order to produce a gRNA expression plasmid, a U6 promoter of wheat and a gRNA scaffold were cloned into a multicloning site of a pTAKN-2 vector. Thereafter, the target sequence of each target gene was introduced into an internal BbsI site, and each gRNA expression plasmid was thus obtained.

```
TaQsd1 target sequence:
                        (SEQ ID NO: 4)
ACGGATCCACCTCCCTGCAGCGG TaLOX2 target sequence:
                        (SEQ ID NO: 5)
GTGCCGCGCGACGAGCTCTTCGG TaGASR7 target sequence:
                        (SEQ ID NO: 6)
CCGCCGGGCACCTACGGCAAC
```

Each gRNA expression plasmid as above, a Cas9 gene expression plasmid, and the GFP expression plasmid (see Example 1-1-(3)) were added at 5 μg, 2.5 μg and 2.5 μg per 750 μg of the gold particles, respectively. The gold particles with a diameter of 0.6 μm were used at 187.5 μg per shot.

(4) Confirmation of Mutagenesis Through Each Target Gene Sequence Cleavage

Individuals in which GFP fluorescence (excitation: 470/40, absorption: 525/50) was observed in the shoot apex under a stereoscopic fluorescence microscope (MZFL III, Leica) were transferred to disposable containers for plant cell culture (Sigma) in which an MS-maltose medium was placed and grown in a long-day condition (22° C., day length of 16 hours). After about a week, the shoot apex of each individual was isolated and placed in an 8-strip PCR tube containing 2 μL of DNAzol Direct (registered trademark, Cosmo Bio), and then a genomic DNA was extracted.

PCR reaction was performed using the genomic DNA as a template with primers produced based on the sequences specific to each of the genes.

```
                        (SEQ ID NO: 7)
TaQsd1-F:    CAGCCTGGAGGGAATGACC (SEQ ID NO: 8)
TaQsd1-R:    ACCTGGTGGAATCCAGAGC (SEQ ID NO: 9)
TaLOX2-F:    CGTCTACCGCTACGACGTCTACAACG (SEQ ID NO: 10)
TaLOX2-R:    GGTCGCCGTACTTGCTCGGATCAAGT (SEQ ID NO: 11)
TaGASR7-F:   CCTTCATCCTTCAGCCATGCAT (SEQ ID NO: 12)
TaGASR7-R:   CCACTAAATGCCTATCACATACG
```

A PCR reaction mixture was prepared by mixing 0.5 μL of the genomic DNA, 0.4 U of KODFX Neo (TOYOBO), 10 μL of accompanying 2× buffer, 0.4 mM dNTPs, and the pair of primers (each 0.2 μM) with sterile distilled water such that the total volume was 20 μl.

In the PCR reaction, the PCR reaction mixture was subjected to 35 cycles of reaction of 98° C. for 10 seconds and 68° C. for 1 minute using TaKaRa PCR Thermal Cycler Dice. After the PCR reaction, 1 μL of each PCR product, 1 μL of accompanying 10× buffer, and 5 U of an appropriate restriction enzyme were mixed with sterile distilled water such that the total volume was 10 μL. After the reaction mixture was reacted at 37° C. overnight, electrophoresis was performed on 2.0% agarose gel, and the gel was stained using ethidium bromide.

Figure 11:
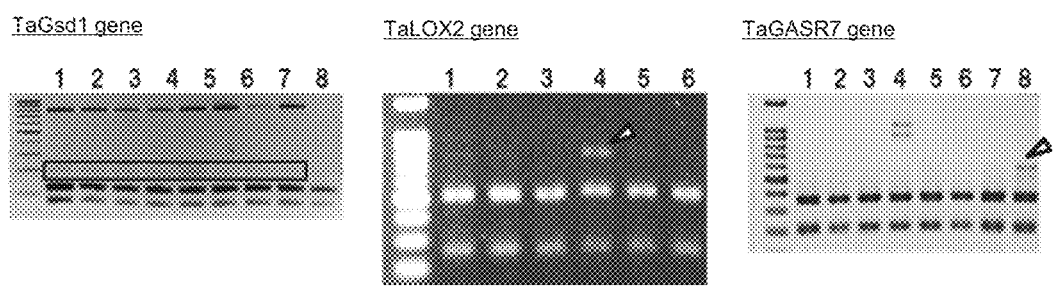
FIG. 11 shows the mutagenesis for the target genes in shoot apexes a week after gene introduction (Example 13).

The PCR products were completely cleaved by the restriction enzyme in the wild-type strain, whereas remaining uncut portion was generated from the PCR products in the mutated individual. A DNA was extracted and purified from the band of the remaining uncut portion, and was sequenced. An individual in which mutation was introduced into the target gene sequence was determined as a target gene-mutated individual (FIG. 11). As a result, for all the target genes, a mutagenesis was confirmed in the cells in the shoot apex a week after the introduction of the genome editing vector.

2. Confirmation of Target Gene Mutagenesis in T$_0$ Generation Adult Leaf and T$_1$ Generation Young Leaf (1) Preparation of Fully Mature Seed of Wheat This was performed in accordance with the method described in Example 13-1-(1).

(2) Exposure of Shoot Apex in Embryo of Fully Mature Seed

This was performed in accordance with the method described in Example 1.3-1-(2).

(3) Gene Introduction

This was performed in accordance with the method described in Example 13-1-(3).

(4) Growth of Transgenic Individual

The transgenic individual that had been left to stand overnight was transferred to a disposable container for plant cell culture (Sigma) in which an MS-maltose medium was placed, and was grown in a long-day condition (22° C., day length of 16 hours). After grown for 2 weeks, the individual was transferred to a pot in which seedling compost for gardening was placed at a time point when the second and third leaves were observed. Thereafter the individual was grown in a long-day condition in a climatic chamber (24° C., day length of 16 hours, humidity of 50 to 70%).

(5) Confirmation of Target Gene Mutagenesis in Leaf of T$_0$ Plant

Whether or not a mutation was introduced into the target gene in the obtained plant body was examined. A genomic DNA was extracted from a fifth leaf or a flag leaf (50 mg) using a benzyl chloride method, and PCR reaction was performed using the genomic DNA as a template with primers produced based on the sequences specific to each of the genes.

A PCR reaction mixture was prepared by mixing 0.7 μL of the genomic DNA 0.4 U of KODFX Neo (TOYOBO), 5 μL of accompanying 2× buffer 0.4 mM dNTPs, and the pair of primers (each 0.2 μM) with sterile distilled water such that the total volume was 10 μl.

In the PCR reaction, the PCR reaction mixture was subjected to 32 cycles of reaction of 98° C. for 10 seconds and 68° C. for 1 minute using TaKaRa PCR Thermal Cycler Dice. PCR/restriction enzyme analysis was performed in accordance with the method described in Example 13-1-(4).

Figure 12:
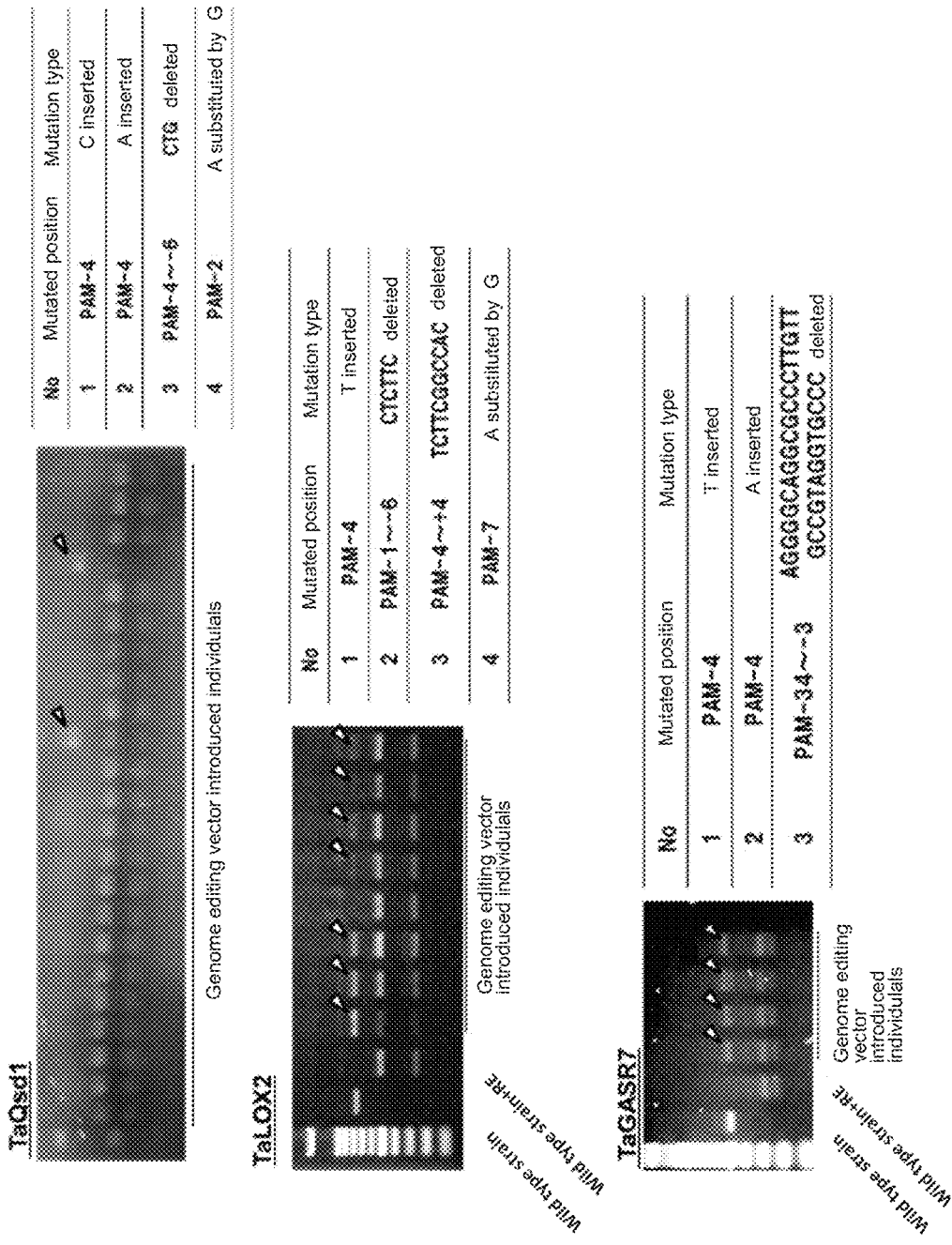
FIG. 12 shows target gene introduced individuals of $T_0$ generation adult leaves (Example 13).

The PCR products were completely cleaved by the restriction enzyme in the wild-type strain, whereas remaining uncut portion was generated from the PCR products in the mutated individual. A DNA was extracted and purified from the band of the remaining uncut portion, and was sequenced. An individual in which a mutation was introduced into the target gene sequence was determined as a target gene-mutated individual. As a result, regarding all the target genes, the target gene mutagenesis was confirmed in the T$_0$ generation adult leaf (FIG. 12, Table 10).

TABLE 10

| Target gene | No. of processed individuals | T$_0$ generation mutated individuals | T$_0$ generation mutagenesis efficiency |
|---|---|---|---|
| TaQsd1 | 243 | 9 | 3.7% |
| TaLOX2 | 240 | 7 | 2.9% |
| TaGASR7 | 210 | 11 | 5.2% |

(6) Confirmation of Target Gene Mutagenesis in Leaf of T$_1$ Plant

Figure 13:
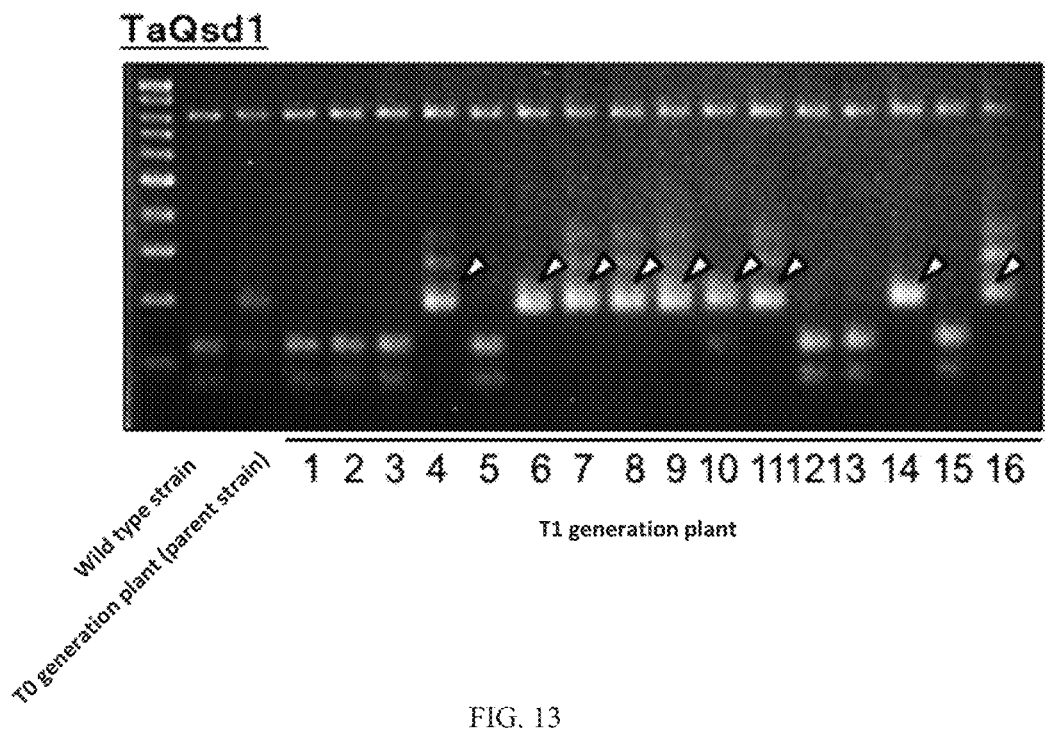
FIG. 13 is a diagram showing the target gene mutagenesis in $T_1$ generation leaves (Example 13).

T$_1$ seeds were collected from the TaQsd1-mutated individual, in which the mutation had been confirmed in (5) above, and a genomic DNA was extracted from a young leaf (50 mg) of a T$_1$ generation plant using a benzyl chloride method. Confirmation of the subsequent target gene mutagenesis was performed in accordance with the method described in (5) above. As a result, regarding two lines of T$_1$ generation, the target gene mutagenesis was confirmed in the T$_1$ young leaf FIG. 13 shows the analysis results from a single line of T$_1$ generation. It was confirmed that mutation was introduced into the target genes in nine individuals out of sixteen individuals. It was found that the gene introduction method can be used to allow genome editing of a shoot apical stem cell that transits to a germ cell line in a shoot apical.

Example 14: Target Mutagenesis Through Cas9 Protein Introduction Using Gene Introduction Method Whether or not genome editing of a target gene present in wheat can be performed through gRNA/Cas9 protein introduction using the gene introduction method was evaluated. In order to conduct this evaluation, a complex of a gRNA targeting a TaLOX2 gene and a Cas9 protein was introduced into a shoot apex of wheat.

1. Confirmation of Target Gene Mutagenesis into a Week after Gene Introduction (1) Preparation of Fully Mature Seed of Wheat This was performed in accordance with the method described in Example 1-1-(1), proviso that fully mature seeds of wheat (*Triticum aestivum* cv. Bobwhite) were used.

(2) Exposure of Shoot Apex in Embryo of Fully Mature Seed

This was performed in accordance with the method described in Example 1-1-(2).

(3) gRNA Cas9 Protein Introduction

The gene introduction into the shoot apex of the fully mature embryo of wheat was performed using a particle bombardment method as described below.

In this example, a mixture (0.5 μg/μL) of a crRNA and a tracrRNA (FASMAC) was used as the gRNA. EnGen Cas9 NLS derived from *Streptococcus pyogenes* (NEB) was used as the Cas9 protein.

crRNA:
(SEQ ID NO: 13)
GUGCCGCGCGACGAGCUCUUguuuuagagcuaugcuguuuug tracrRNA:
(SEQ ID NO: 14)
AAACAGCAUAGCAAGUUAAAUAAGGCUAGUCCGUUAUCAACUUGAAAAAG
UGGCACCGA GUCGGUGCU With sterile distilled water 4 μg of each gRNA as above, 7 μg of the Cas9 protein, 2 μL of 10× Cas9 buffer, and 0.5 μL of Ribolock RNase Inhibitor were mixed such that the total volume was 20 μL. After the mixture was left to stand at room temperature for 15 minutes, 750 μg or 1500 μg of gold particles was added thereto, and the resultant mixture was left to stand on ice for 10 minutes. After the supernatant was discarded, 2.5 μg of the GFP expression plasmid (see Example 1-1-(3)) and 32 μL of sterile distilled water were added, and this was used together with a gold particle/Cas9 complex. The gold particles with a diameter of 0.6 μm were used at 187.5 or 375 μg per shot, and the bombardment was performed at 4 shots per plate. A hydrophilic film (SH2CLHF, 3 M) cut into 1.0 to 1.5 cm square was attached to the center of a macrocarrier in a clean bench. Then, 8 μL of the above-mentioned gold particle/Cas9 complex was poured thereonto, and the macrocarrier was air-dried. Bombardment was performed in the conditions described in Example 1-1-(3).

(4) Confirmation of Mutagenesis Through TaLOX2 Target Gene Sequence Cleavage

The analysis was performed in accordance with the method described in Example 13-1-(4).

Figure 14:
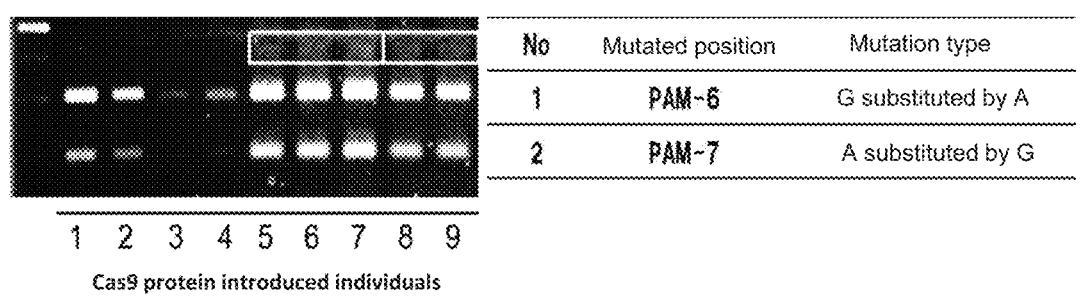
FIG. 14 is a diagram showing target gene introduced individuals obtained through direct introduction of a Cas9 protein (Example 14).

When the hydrophilic film was not used, GFP fluorescence was not observed in the shoot apex, whereas when the hydrophilic film was used, GFP fluorescence was observed (Table 11). Furthermore, when the amount of the gold particles per shot was increased from 187.5 µg to 375 µg, the expression efficiency of GFP fluorescence was enhanced from 23.3% to 66.7% (Table 11). It was found that by use of the hydrophilic film, the gold particles suspended in an aqueous solvent was efficiently introduced into the shoot apex. As a result of performing the PCR/restriction enzyme analysis on the individual in which GFP fluorescence was observed in accordance with Example 13-1-(4), the PCR products were completely cleaved by the restriction enzyme in the wild-type strain, whereas remaining uncut portion was generated from the PCR products in the mutated individual, A DNA was extracted and purified from the band of the uncut portion, and was sequenced. As a result, it was confirmed that mutation was introduced into the target gene sequence (FIG. 14). As a result, for TaLOX2 target gene, a mutagenesis was confirmed in the cells in the shoot apex a week after the introduction of the gRNA/Cas9 protein.

TABLE 11

Enhancement of gold particle introduction efficiency by hydrophilic film

| Gold particle (µg) | Film | No. of processed individuals | No. of individuals expressing GFP in shoot apex | Efficiency of expressing GFP in shoot apex (%) |
|---|---|---|---|---|
| 187.5 | Macrocarrier | 30 | 0 | 0.0 |
| 187.5 | Hydrophilic film | 30 | 7 | 23.3 |
| 375.0 | Hydrophilic film | 30 | 20 | 66.7 |

Example 15: Target Mutagenesis into Soybean Using Gene Introduction Method

A target gene-mutated individual of soybean can also be obtained using substantially the same method as the method used to obtain that of wheat.

1. Preparation of Fully Mature Seeds of Soybean

Samples are prepared using fully mature seeds of soybean (Fukuyutaka and Enrei) in accordance with the method described in Example 7-1-(1).

2. Exposure of Shoot Apex in Embryo of Fully Mature Seed

This is performed in accordance with the method described in Example 7-1-(2).

3. Gene Introduction

The gene introduction into the shoot apex of the fully mature embryo was performed using a particle bombardment method as described below.

In this example, in order to produce a gRNA expression plasmid, a U6 promoter of soybean and a gRNA scaffold are cloned into a multicloning site of a pTAKN-2 vector. Thereafter, a target sequence of target gene is introduced into an internal BbsI site, and each gRNA expression plasmid is thus obtained.

```
Glyma. 10G244400.1 target sequence:
                                (SEQ ID NO: 15)
CCTCCGCCCAAGGCTCCGCCACC Glyma. 20G150000.1 target sequence:
                                (SEQ ID NO: 15)
CCTCCGCCCAAGGCTCCGCCACC
```

Each gRNA expression plasmid as above, a Cas9 gene expression plasmid, and the GFP expression plasmid (see Example 7-1-(3)) are added at 5 µg, 2.5 µg and 2.5 µg per 750 µg of the gold particles, respectively. The gold particles with a diameter of 0.6 µm are used at 187.5 µg per shot.

4. Selection Using Transient Expression of GFP Protein as Index

Individuals in which GFP fluorescence (excitation: 470/40, absorption: 525/50) is observed in the shoot apex under a stereoscopic fluorescence microscope (MZFL III, Leica) are transferred to disposable containers for plant cell culture (Sigma) in which an RPM medium (4.3 g/L MS salt, MS vitamin, 3% sucrose, 0.50 g/L MES, 3% PPM (plant preservative mixture; Nacalai Tesque inc.), 0.3% Gelrite, pH 5.7) is placed, and grown in an incubator (23° C., day length of 16 hours).

5. Growth of Transgenic Individual

This is performed in accordance with the method described in Example 7-2-(1).

6. Confirmation of Target Gene Mutagenesis in Leaf of $T_0$ Plant

Whether or not mutation is introduced into the target gene in the obtained plant body is examined. A genomic DNA is extracted from a newly grown leaf (50 mg) using a benzyl chloride method, and PCR reaction is performed using the genomic DNA as a template with primers produced based on the sequences specific to each gene. PCR/restriction enzyme analysis is performed in accordance with the method described in Example 13-1-(4). The mutated individual is grown sequentially and seeds of next generation are obtained, thus making it possible to obtain a stable target gene-mutated individual.

Example 16: Target Mutagenesis into Soybean Through Cas9 Protein Introduction Using Gene Introduction Method A target gene-mutated individual of soybean can also be obtained using substantially the same method as the method used to obtain that of wheat. For example, a complex of a gRNA targeting a Glyma.10G244400.1 gene and a Cas9 protein is introduced into a shoot apex.

1. Preparation of Fully Mature Seeds of Soybean

This is performed in accordance with the method described in Example 15-1.

2. Exposure of Shoot Apex in Embryo of Fully Mature Seed

This is performed in accordance with the method described in Example 15-2.

3. gRNA/Cas9 Protein Introduction

The gene introduction into the shoot apex of the fully mature embryo of soybean is performed using a particle bombardment method as described below.

In this example, a mixture (0.5 µg/µL) of a crRNA and a tracrRNA (FASMAC) is used as the gRNA. EnGen Cas9 NLS derived from *Streptococcus pyogenes* (NEB) is used as the Cas9 protein.

```
crRNA:
                                        (SEQ ID NO: 16)
GGUGGCGGAGCCUUGGGCGGguuuuagagcuaugcuguuug tracrRNA:
                                        (SEQ ID NO: 14)
AAACAGCAUAGCAAGUUAAAAUAAGGCUAGUCCGUUAUCAAC

UUGAAAAGUGGCACCGA GUCGGUGCU
```

Bombardment is performed in accordance with the conditions of the method described in Example 14-1-(3).

4. Selection Using Transient Expression of GFP Protein as Index

This is performed in accordance with the method described in Example 15-4.

5. Growth of Transgenic Individual

This is performed in accordance with the method described in Example 15-5.

6. Confirmation of Target Gene Mutagenesis in Leaf of $T_0$ Plant

A stable target gene-mutated individual can be produced in accordance with the method described in Example 15-6.

Example 17: Target Mutagenesis into Rice Through Cas9 Protein Introduction Using Gene Introduction Method A target gene-mutated individual of rice can also be obtained using substantially the same method as the method used to obtain that of wheat. For example, a complex of a gRNA targeting an OsPDS (rice phytoene desaturase) gene and a Cas9 protein is introduced into a shoot apex of rice.

1. Preparation of Fully Mature Seeds of Rice

This is performed in accordance with the method described in Example 10-1.

2. Exposure of Shoot Apex in Embryo of Fully Mature Seed

This is performed in accordance with the method described in Example 10-2.

3. gRNA/Cas9 Protein Introduction

The gene introduction into the shoot apex of the fully mature embryo of rice is performed using a particle bombardment method as described below.

In this example, a mixture (0.5 μg/μL) of a crRNA and a tracrRNA (FASMAC) is used as the gRNA. EnGen Cas9 NLS derived from *Streptococcus pyogenes* (NEB) is used as the Cas9 protein.

```
crRNA:
                                        (SEQ ID NO: 17)
GUUGGUCUUGCUCCUGCAGguuuuagagcuaugcuguuug tracrRNA:
                                        (SEQ ID NO: 14)
AAACAGCAUAGCAAGUUAAAAUAAGGCUAGUCCGUUAUCAA

CUUGAAAAGUGGCACCGA GUCGGUGCU
```

Bombardment is performed in accordance with the conditions of the method described in Example 14-1-(3).

4. Selection Using Transient Expression of GFP Protein as Index

This is performed in accordance with the method described in Example 10-4.

5. Growth of Transgenic Individual

This is performed in accordance with the method described in Example 10-5.

6. Confirmation of Target Gene Mutagenesis in Leaf of $T_0$ Plant

A stable target gene-mutated individual can be produced in accordance with the method described in Example 15-6.

Example 18: Target Mutagenesis into Apple Through Cas9 Protein Introduction Using Gene Introduction Method A target gene-mutated individual of apple can also be obtained using substantially the same method as the method used to obtain that of wheat. For example, a complex of a gRNA targeting an apple PDS (phytoene desaturase) gene and a Cas9 protein is introduced into a shoot apex of apple.

1. Preparation of Shoot Apex of Apple

This is performed in accordance with the method described in Example 11-1.

2. Exposure of Shoot Apex

This is performed in accordance with the method described in Example 11-2.

3. gRNA/Cas9 Protein Introduction

The gene introduction into the shoot apex of apple is performed using a particle bombardment method as described below.

In this example, a mixture (0.5 μg/μL) of a crRNA and a tracrRNA (FASMAC) is used as the gRNA. EnGen Cas9 NLS derived from *Streptococcus pyogenes* (NEB) is used as the Cas9 protein.

```
crRNA:
                                        (SEQ ID NO: 18)
ACCUGAUCGAGUAACUACAGguuuuagagcuaugcuguuug tracrRNA:
                                        (SEQ ID NO: 14)
AAACAGCAUAGCAAGUUAAAAUAAGGCUAGUCCGUUAUCAAC

UUGAAAAGUGGCACCGA GUCGGUGCU
```

Bombardment is performed in accordance with the conditions of the method described in Example 14-1-(3), proviso that the GFP vector described in Example 7-1-(0.3) is used.

4. Selection Using Transient Expression of GFP Protein as Index

This is performed in accordance with the method described in Example 11-4.

5. Growth of Transgenic Individual

This is performed in accordance with the method described in Example 11-5.

6. Confirmation of Target Gene Mutagenesis in Leaf of $T_0$ Plant

A stable target gene-mutated individual can be produced in accordance with the method described in Example 15-6.

Example 19: Target Mutagenesis into Potato Through Cas9 Protein Introduction Using Gene Introduction Method A target gene-mutated individual of potato can also be obtained using substantially the same method as the method used to obtain that of wheat. For example, a complex of a gRNA targeting an StIAA2 (an Auxin/Indole-3-Acetic Acid family member) gene and a Cas9 protein is introduced into a shoot apex of potato.

1. Preparation of Shoot Apex of Potato

This is performed in accordance with the method described in Example 9-1.

2. Exposure of Shoot Apex

This is performed in accordance with the method described in Example 9-2.

3. gRNA/Cas9 Protein Introduction

The gene introduction into the shoot apex of potato is performed using a particle bombardment method as described below.

In this example, a mixture (0.5 µg/µL) of a crRNA and a tracrRNA (FASMAC) is used as the gRNA. EnGen Cas9 NLS derived from *Streptococcus pyogenes* (NEB) is used as the Cas9 protein.

```
crRNA:
                                      (SEQ ID NO: 19)
GAUGUUUAGCUCCUUUACUAguuuuagagcuaugcuguuuug tracr:
                                      (SEQ ID NO: 14)
AAACAGCAUAGCAAGUUAAAAUAAGGCUAGUCCGUUAUCAAC

UUGAAAAAGUGGCACCGA GUCGGUGCU
```

Bombardment is performed in accordance with the conditions of the method described in Example 14-1-(3), proviso that the GFP vector described in Example 7-1-(3) is used.

4. Selection Using Transient Expression of GFP Protein as Index

This is performed in accordance with the method described in Example 9-4.

5. Growth of Transgenic Individual

This is performed in accordance with the method described in Example 1-2-(4).

6. Confirmation of Target Gene Mutagenesis in Leaf of $T_0$ Plant

A stable target gene-mutated individual can be produced in accordance with the method described in Example 15-6.

Example 20: Target Mutagenesis into Corn Through Cas9 Protein Introduction Using Gene Introduction Method A target gene-mutated individual of corn can also be obtained using substantially the same method as the method used to obtain that of wheat. For example, a complex of a gRNA targeting a ZmALS2 (corn acetolactate synthase) gene and a Cas9 protein is introduced into a shoot apex of corn.

1. Preparation of Shoot Apex of Corn

This is performed in accordance with the method described in Example 6-1-(1).

2. Exposure of Shoot Apex

This is performed in accordance with the method described in Example 6-1-(2).

3. gRNA/Cas9 Protein Introduction

The gene introduction into the shoot apex of corn is performed using a particle bombardment method as described below.

In this example, a mixture (0.5 µg/µL) of a crRNA and a tracrRNA (FASMAC) is used as the gRNA. EnGen Cas9 NLS derived from *Streptococcus pyogenes* (NEB) is used as the Cas9 protein.

```
crRNA:
                                      (SEQ ID NO: 20)
GCUGCUCGAUUCCGUCCCCAguuuuagagcuaugcuguuuug tracrRNA:
                                      (SEQ ID NO: 14)
AAACAGCAUAGCAAGUUAAAAUAAGGCUAGUCCGUUAUCAAC

UUGAAAAGUGGCACCGA GUCGGUGCU
```

Bombardment is performed in accordance with the conditions of the method described in Example 14-1-(3).

4. Selection Using Transient Expression of GFP Protein as Index

In accordance with the method described in Example 1-1-(4), an individual in which GFP fluorescence is observed in the shoot apex tissue is selected from the individuals subjected to the transformation process using the gold particles with a diameter of 0.6 µm.

5. Growth of Transgenic Individual

This is performed in accordance with the method described in Example 1-2-(4).

6. Confirmation of Target Gene Mutagenesis in Leaf of $T_0$ Plant

A stable target gene-mutated individual can be produced in accordance with the method described in Example 15-6.

Example 21: Target Mutagenesis into Barley Through Cas9 Protein Introduction Using Gene Introduction Method A target gene-mutated individual of barley can also be obtained using substantially the same method as the method used to obtain that of wheat. For example, a complex of a gRNA targeting an HvPM19 (barley ABA-inducible plasma membrane protein) gene and a Cas9 protein is introduced into a shoot apex of barley.

1. Preparation of Shoot Apex of Barley

This is performed in accordance with the method described in Example 8-1-(1).

2. Exposure of Shoot Apex

This is performed in accordance with the method described in Example 8-1-(2).

3. gRNA/Cas9 Protein Introduction

The gene introduction into the shoot apex of barley is performed using a particle bombardment method as described below.

In this example a mixture (0.5 µg/µL) of a crRNA and a tracrRNA (FASMAC) is used as the gRNA. EnGen Cas9 NLS derived from *Streptococcus pyogenes* (NEB) is used as the Cas9 protein.

```
crRNA:
                                      (SEQ ID NO: 21)
GCUCUCCACUCUGGGCUCUUguuuuagagcuaugcuguuuug tracrRNA:
                                      (SEQ ID NO: 14)
AAACAGCAUAGCAAGUUAAAAUAAGGCUAGUCCGUUAUCAAC

UUGAAAAGUGGCACCGA GUCGGUGCU
```

Bombardment is performed in accordance with the conditions of the method described in Example 14-1-(3).

4. Selection Using Transient Expression of GFP Protein as Index

In accordance with the method described in Example 1-1-(4), an individual in which GFP fluorescence is observed in the shoot apex tissue is selected from the individuals subjected to the transformation process using the gold particles with a diameter of 0.6 μm.

5. Growth of Transgenic Individual

This is performed in accordance with the method described in Example 1-2-(4).

6. Confirmation of Target Gene Mutagenesis in Leaf of $T_0$ Plant

A stable target gene-mutated individual can be produced in accordance with the method described in Example 15-6.

One or more embodiments of the present invention can be applied to the agricultural industry pharmaceutical industry, and enzyme industry.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

LIST OF REFERENCE NUMERALS

Al Aleurone layer
E Endosperm

What is claimed is:

1. A method for editing a plant genome, comprising:
coating a microparticle with a protein, wherein the protein comprises a nuclease or a deaminase;
coating a hydrophilic macrocarrier film with the resulting protein-coated microparticle,
wherein the hydrophilic macrocarrier film is a film formed by attaching a hydrophilic film to a macrocarrier film or by applying a hydrophilic coating onto the macrocarrier film,
introducing a deletion, an insertion, or a substitution into a target site in the plant genome by bombarding a shoot apex of the plant using the hydrophilic macrocarrier film coated with the protein-coated microparticle using a gene gun,
wherein in the bombarding,
the protein-coated microparticle is bombarded onto the plant, and
the shoot apex of the plant is a shoot apex of an embryo of a fully mature seed or a shoot apex of a young bud of a tuber;
growing the shoot apex bombarded with the protein-coated microparticle without applying selective pressure so as to obtain a plant body; and
selecting a genome-edited plant body from the plant body,
wherein efficiency of editing the plant genome is increased compared with efficiency obtained by a same method other than that the hydrophilic macrocarrier film is not used.

2. The method according to claim 1, wherein the fully mature seed is a fully mature seed comprising a root having a length of 1 mm or less.

3. The method according to claim 1, wherein the plant is selected from the group consisting of wheat, barley, rice, corn, soybean, potato, and apple.

4. The method according to claim 1, wherein the coating the microparticle is performed by coating the microparticle with the nuclease as the protein.

5. The method according to claim 4, wherein the nuclease is a Cas nuclease.

6. The method according to claim 1, further comprising growing the genome-edited plant body.

7. The method according to claim 1, wherein the genome is in a germ cell line or a stem cell that can differentiate into the germ cell line in a shoot apical meristem, and wherein the method is an in planta method.

8. The method according to claim 7, further comprising growing the genome-edited plant body.

9. The method according to claim 1, wherein the coating the microparticle is performed by coating the microparticle with the deaminase as the protein.

10. The method according to claim 1, wherein a number of shots for bombarding the shoot apex of the plant with the protein-coated microparticle is two or more.

11. The method according to claim 1, wherein in the bombarding, a stopping plate is set on the gene gun so that a distance between the stopping plate and the shoot apex is in a range of 6 cm or less.

12. The method according to claim 1, further comprising exposing the shoot apex of the plant by removing tissues,
wherein the tissues removed in the exposing the shoot apex are:
(i) for the embryo of the fully mature seed, an endosperm, a coleoptile, a leaf primordium, and an excess of a scutellum of the fully mature seed; or
(ii) for the shoot apex of the young bud of the tuber, a tuber and a leaf primordium of the young bud of the tuber.

13. The method according to claim 1, wherein the protein-coated microparticle is further coated with a nucleic acid.

14. The method according to claim 13, wherein the nucleic acid encodes a nuclease or a deaminase.

15. The method according to claim 1, wherein the introducing the deletion, the insertion, or the substitution is performed by bombarding a L2 layer cell in the shoot apex with the protein-coated microparticle.

16. The method according to claim 1, wherein in the introducing the deletion, the insertion, or the substitution is performed by bombarding a shoot apical stem cell that differentiates into a germ cell line in the shoot apex.

17. The method according to claim 1, wherein the microparticle to be coated with the protein has a diameter in a range from 0.3 to 1.5 μm.

18. The method according to claim 12, wherein the shoot apex of the plant is the shoot apex of the embryo of the fully mature seed.

19. The method according to claim 12, wherein the shoot apex of the plant is the shoot apex of the young bud of the tuber.

20. The method according to claim 13, wherein the coating the microparticle is performed by coating the microparticle with nucleic acids each linked to a promoter and a terminator, and
    wherein the nucleic acids comprise a nucleic acid capable of expressing at least one guide RNA and a nucleic acid encoding a Cas nuclease protein.

\* \* \* \* \*